(12) United States Patent
Shaw et al.

(10) Patent No.: US 7,049,128 B2
(45) Date of Patent: May 23, 2006

(54) PLATELET GLYCOPROTEIN IBα FUSION POLYPEPTIDES AND METHODS OF USE THEREOF

(75) Inventors: Gray D. Shaw, Milton, MA (US);
Dianne S. Sako, Medford, MA (US);
Ravindra Kumar, Acton, MA (US);
Francis Sullivan, Belmont, MA (US);
Tom McDonagh, Acton, MA (US)

(73) Assignee: Genetics Institute LLC, Cambridge, MA (US)

( * ) Notice: Subject to any disclaimer, the term of this patent is extended or adjusted under 35 U.S.C. 154(b) by 145 days.

(21) Appl. No.: 10/382,758

(22) Filed: Mar. 6, 2003

(65) Prior Publication Data

US 2003/0232047 A1    Dec. 18, 2003

Related U.S. Application Data

(62) Division of application No. 10/068,426, filed on Feb. 6, 2002.

(60) Provisional application No. 60/266,838, filed on Feb. 6, 2001.

(51) Int. Cl.
*C12N 15/00* (2006.01)
*C12N 1/20* (2006.01)
*C12N 15/87* (2006.01)
*C07H 21/04* (2006.01)
*A61K 48/00* (2006.01)

(52) U.S. Cl. ............ 435/252.3; 435/325; 435/455; 435/320.1; 536/23.5; 514/44

(58) Field of Classification Search ............ 536/23.5; 435/320.1, 325, 455, 252.3; 514/44
See application file for complete search history.

(56) References Cited

U.S. PATENT DOCUMENTS

| | | |
|---|---|---|
| 5,225,538 A | 7/1993 | Capon et al. |
| 5,340,727 A | 8/1994 | Ruggeri et al. |
| 5,428,130 A | 6/1995 | Capon et al. |
| 5,455,165 A | 10/1995 | Capon et al. |
| 5,514,582 A | 5/1996 | Capon et al. |
| 5,516,964 A | 5/1996 | Umansky et al. |
| 5,593,959 A | 1/1997 | Miller et al. |
| 5,714,147 A | 2/1998 | Capon et al. |
| 6,136,310 A | 10/2000 | Hanna et al. |
| 6,177,059 B1 | 1/2001 | Matsuda et al. |
| 6,277,975 B1 | 8/2001 | Larsen et al. |

FOREIGN PATENT DOCUMENTS

| | | |
|---|---|---|
| EP | 0317278 | 11/1988 |
| EP | 1 074 564 | 2/2001 |
| WO | WO 98/08949 | 3/1998 |
| WO | WO 99/51642 | 10/1999 |

OTHER PUBLICATIONS

Dong, et al. (2000). J. Biol. Chem. 275: 27663-27670.
GenBank Accession No.: BAB12083 (Aug. 26, 2000).

(Continued)

*Primary Examiner*—Christina Chan
*Assistant Examiner*—Maher Haddad
(74) *Attorney, Agent, or Firm*—Ivor R. Elrifi; David E. Johnson; Mintz Levin

(57) ABSTRACT

The present invention provides compositions and methods for treating or preventing vascular-associated disorders.

8 Claims, 6 Drawing Sheets

OTHER PUBLICATIONS

GenBank Accession No.: AB038516 (Aug. 25, 2000).
GenBank Accession No.: BAA12911 (Apr. 14, 2000).
GenBank Accession No.: AAC53320 (Aug. 17, 1997).
GenBank Accession No.: U91967 (Aug. 17, 1997).
Lopez, et al. (1987). Proc. Natl. Acad. Sci. USA 84: 5615-5619.
Titani, et al. (1987). Proc. Natl. Acad. Sci. USA 84: 5610-5614.
Attwood *Science*, 290(5491):471-473 (2000).
Cole et al. *J. Immunol.*, 59(7):3613-3621 (1997).
Geneseq Online Database Accession No: AAY49933 (Feb. 1, 2000).
Metzler et al. *Nat. Struc. Biol.*, 4(7):527-531 (1997).
Miura et al. *J. Biol. Chem.*, 275(11):7539-7546 (2000).
Ngo et al. Computational Complexity, Protein Structure Prediction, and the Levinthal Paradox in the Protein Folding Problem, Birkhauser, 14:435-508 (1994).
Scalia et al. *Circ. Res.*, 84(1):93-102 (1999).
Skolnick et al. *Trends Biotechnol.*, 18(1):34-39 (2000).

PLATELET GLYCOPROTEIN IBα FUSION POLYPEPTIDES AND METHODS OF USE THEREOF

RELATED U.S. APPLICATION

The present application is a divisional application of, and claims priority to, U.S. Ser. No. 10/068,426, filed Feb. 6, 2002 now allowed, which claims priority to U.S. Ser. No. 60/266,838, filed Feb. 6, 2001 to which the present application also claims priority. The contents of these applications are incorporated herein by reference in their entireties.

FIELD OF THE INVENTION

The invention relates to generally to compositions and methods for treating or preventing vascular-associated disorders and more particularly to compositions including platelet glycoprotein IBα-derived polypeptides and methods of using same.

BACKGROUND OF THE INVENTION

The deleterious effects of vascular-associated disorders such as stroke, heart attack, and artheroseclerosis are thought to be caused, at least in part, by the inappropriate triggering of a vascular inflammation and repair response. The vascular inflammation and repair response involves adhesive interactions between various cell types normally found freely circulating in blood. Examples of such interactions the interaction that can occur between platelets, leukocytes and the inner wall of blood vessels (i.e., the vascular endothelium). Under conditions of high fluid shear forces, platelets adhere to the endothelium via an interaction between the glycoprotein (GP) Ib-IX-V complex on their surface and von Willebrand factor (vWF) present on exposed vessel subendothelium. In contrast, leukocytes can adhere either directly to activated endothelium or indirectly by first adhering to vWF-immobilized platelets. In both instances, leukocyte cell surface molecules that bind to either the selectins or integrins classes of adhesion receptors mediate these adhesion events. Leukocyte-platelet adhesion is thought to occur, in part, via interaction of the leukocyte surface integrin molecule, MacI and the GP1b component of the platelet surface GP1b-IX-V complex.

In response to vascular disturbances such as artherosclerotic plaque rupture or mechanical injury, e.g., such as that caused by angioplasty, stent placement, ischemic damage or stenosis, leukocytes and platelets can accumulate at a vascular lesion site and provide multiple adhesive substrates for one another. This accumulation of leukocytes and platelets lead to the local production of factors including, e.g., mitogens, cytokines and chemokines, causing the further undesirable progression of a vascular disease.

SUMMARY OF THE INVENTION

The invention is based in part on the discovery of glycoprotein-Ibα-derived fusion proteins that inhibit the adherence of platelets to leukocytes. Accordingly, the glycoprotein-Ibα-derived fusion proteins can be used to treat vascular conditions associated with vascular inflammation, thrombosis, atherosclerosis, and angioplasty-related restenosis. The polypeptides, referred to herein as glycoprotein Ibα fusion polypeptides.

In one aspect, the invention provides a glycoprotein Ibα fusion polypeptide that includes a first polypeptide, comprising at least a region of a glycoprotein Ibα polypeptide, operably linked to a second polypeptide. The second polypeptide is preferably to form a multimer, e.g., a dimer. In preferred embodiments, the second polypeptide comprising at least a region of an immunoglobulin polypeptide. In some embodiments, the fusion protein includes the sequences of GP1b302-Ig (SEQ ID NO:1), Gp1b302/2A-Ig (SEQ ID NO:2), GP1b302/4X-Ig (SEQ ID NO:3), GP1b290 Ig (SEQ ID NO:4), GP1b290/2V-Ig (SEQ ID NO:5), or GP1b290/1A-Ig (SEQ ID NO:6), or a fragment, homolog, analog or derivative thereof. The sequences of these polypeptides are provided below:

```
GP1b302/Ig
MPLLLLLLLLPSPLHPHPICEVSKVASHLEVNCDKRNLTALPPDLPKDTTILHLSENLLYTFSLA    (SEQ ID NO:1)

TLMPYTRLTQLNLDRCELTKLQVDGTLPVLGTLDLSHNQLQSLPLLGQTLPALTVLDVSFNRLTS

LPLGALRGLGELQELYLKGNELKTLPPGLLTPTPKLEKLSLANNNLTELPAGLLNGLENLDTLLL

QENSLYTIPKGFFGSHLLPFAFLHGNPWLCNCEILYFRRWLQDNAENVYVWKQGVDVKAMTSNVA

SVQCDNSDKFPVYKYPGKGCPTLGDEGDTDLYDYYPEEDTEGDKVRATRTVVKFPTKARPHTCPP

CPAPEALGAPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPVPIEKTISKAKGQPREPQVYTLPPSREEM

TKNQVSLTCLVKGFYPSDIAVEWESNGQPENNYKTTPPVLDSDGSFFLYSKLTVDKSRWQQGNVF

SCSVMHEALHNHYTQKSLSLSPGK

GP1b302/2A-Ig
MPLLLLLLLLPSPLHPHPICEVSKVASHLEVNCDKRNLTALPPDLPKDTTILHLSENLLYTFSLA    (SEQ ID NO:2)

TLMPYTRLTQLNLDRCELTKLQVDGTLPVLGTLDLSHNQLQSLPLLGQTLPALTVLDVSFNRLTS

LPLGALRGLGELQELYLKGNELKTLPPGLLTPTPKLEKLSLANNNLTELPAGLLNGLENLDTLLL

QENSLYTIPKGFFGSHLLPFAFLHGNPWLCNCEILYFRRWLQDNAENVYVWKQGVDVKAMTSNVA

SVQCDNSDKFPVYKYPGKGCPTLGDEGDTDLYDYYPEEDTEGDKVAATATVVKFPTKARPHTCPP
```

-continued

```
CPAPEALGAPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPVPIEKTISKAKGQPREPQVYTLPPSREEM

TKNQVSLTCLVKGFYPSDIAVEWESNGQPENNYKTTPPVLDSDGSFFLYSKLTVDKSRWQQGNVF

SCSVMHEALHNHYTQKSLSLSPGK

GP1b3O2/4X-Ig
MPLLLLLLLLPSPLHPHPICEVSKVASHLEVNCDKRNLTALPPDLPKDTTILHLSENLLYTFSLA      (SEQ ID NO:3)

TLMPYTRLTQLNLDRCELTKLQVDGTLPVLGTLDLSHNQLQSLPLLGQTLPALTVLDVSFNRLTS

LPLGALRGLGELQELYLKGNELKTLPPGLLTPTPKLEKLSLANNNLTELPAGLLNGLENLDTLLL

QENSLYTIPKGFFGSHLLPFAFLHGNPWLCNCEILYFRRWLQDNAENVYVWKQVVDVKAVTSNVA

SVQCDNSDKFPVYKYPGKGCPTLGDECDTDLYDYYPEEDTEGDKVAATATVVKFPTKARPHTCPP

CPAPEALGAPSVFLFPPKPKDTLMISRTPEVTCVVVDVSHEDPEVKPNWYVDGVEVHNAKTKPRE

EQYNSTYRVVSVLTVLHQDWLNGKEYKCKVSNKALPVPIEKTISKAKGQPREPQVYTLPPSREEM

TKNQVSLTCLVKGFYPSDIAVEWESNGQPENNYKTTPPVLDSDGSFFLYSKLTVDKSRWQQGNVF

SCSVMHEALHNHYTQKSLSLSPGK

GPYb290-Ig
MPLLLLLLLLPSPLHPHPICEVSKVASHLEVNCDKRNLTALPPDLPKDTTILHLSENLLYTFSLA      (SEQ ID NO:4)

TLMPYTRLTQLNLDRCELTKLQVDGTLPVLGTLDLSHNQLQSLPLLGQTLPALTVLDVSFNRLTS

LPLGALRGLGELQELYLKGNELKTLPPGLLTPTPKLEKLSLANNNLTELPAGLLNGLENLDTLLL

QENSLYTIPKGFFGSHLLPFAFLHGNPWLCNCEILYFRRWLQDNAENVYVWKQGVDVKAMTSNVA

SVQCDNSDKFPVYKYPGKGCPTLGDEGDTDLYDYYPEEDTEGDKVRPHTCPPCPAPEALGAPSVF

LFPPKPKDTLMISRTPEVTCVVVDVSHEDPEVKFNWYVDGVEVHNAKTKPREEQYNSTYRVVSVL

TVLHQDWLNGKEYKCKVSNKALPVPIEKTISKAKGQPREPQVYTLPPSREEMTKNQVSLTCLVKG

FYPSDIAVEWESNGQPENNYKTTPPVLDSDGSFFLYSKLTVDKSRWQQGNVFSCSVMHEALHNHY

TQKSLSLSPGK

GP1b290/2V-Ig
MPLLLLLLLLPSPLHPHPICEVSKVASHLEVNCDKRNLTALPPDLPKDTTILHLSENLLYTFSLA      (SEQ ID NO:5)

TLMPYTRLTQLNLDRCELTKLQVDGTLPVLGTLDLSHNQLQSLPLLGQTLPALTVLDVSFNRLTS

LPLGALRGLQELQELYLKGNELKTLPPGLLTPTPKLEKLSLANNNLTELPAGLLNGLENLDTLLL

QENSLYTIPKGFFGSHLLPFAFLHGNPWLCNCEILYFRRWLQDNAENVYVWKQVVDVKAVTSNVA

SVQCDNSDKFPVYKYPGKGCPTLGDEGDTDLYDYYPEEDTEGDKVRPHTCPPCPAPEALGAPSVF

LFPPKPKDTLMISRTPEVTCVVVDVSHEDPEVKFNWYVDGVEVHNAKTKPREEQYNSTYRVVSVL

TVLHQDWLNGKEYKCKVSNKALPVPIEKTISKAKGQPREPQVYTLPPSREEMTKNQVSLTCLVKG

FYPSDIAVEWESNCQPENNYKTTPPVLDSDGSFFLYSKLTVDKSRWQQGNVFSCSVMHEALHNHY

TQKSLSLSPGK

GP1b290/1A-Ig
MPLLLLLLLLPSPLHPHPICEVSKVASHLEVNCDKRNLTALPPDLPKDTTILHLSENLLYTFSLA      (SEQ ID NO:6)

TLMPYTRLTQLNLDRCELTKLQVDGTLPVLGTLDLSHNQLQSLPLLGQTLPALTVLDVSFNRLTS

LPLGALRGLGELQELYLKGNELKTLPPGLLTPTPKLEKLSLANNNLTELPAGLLNGLENLDTLLL

QENSLYTIPKGFFGSHLLPFAFLHGNPWLCNCEILYFRRWLQDNAENVYVWKQGVDVAAMTSNVA

SVQCDNSDKFPVYKYPGKGCPTLGDEGDTDLYDYYPEEDTEGDKVRPHTCPPCPAPEALGAPSVF

LFPPKPKDTLMISRTPEVTCVVVDVSHEDPEVKFNWYVDGVEVHNAKTKPREEQYNSTYRVVSVL

TVLHQDWLNGKEYKCKVSNKALPVPIEKTISKAKGQPREPQVYTLPPSREEMTKNQVSLTCLVKG
```

-continued

```
FYPSDIAVEWESNGQPENNYKTTPPVLDSDGSFFLYSKLTVDKSRWQQGNVFSCSVMHEALHNHY

TQKSLSLSPGK
```

Also provided by the invention is a method of inhibiting leukocyte adhesion to a biological tissue contacting a leukocyte with a glycoprotein Ibα fusion polypeptide according to the invention. The leukocyte is contacted in an amount sufficient to inhibit adherence of the leukocyte and the biological tissue In another aspect, the invention provides a method of treating a disorder associated with platelet activation. The method includes administering to a subject an effective amount of a glycoprotein Ibα fusion polypeptide.

Also included in the invention is a nucleic acid encoding a glycoprotein Ibα fusion polypeptide, as well as a vector containing glycoprotein Ibα fusion polypeptide-encoding nucleic acids described herein, and a cell containing the vectors or nucleic acids described herein.

Also included in the invention are pharmaceutical compositions that include the glycoprotein Ibα fusion polypeptides, as well as antibodies that specifically recognize the glycoprotein Ibα fusion polypeptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
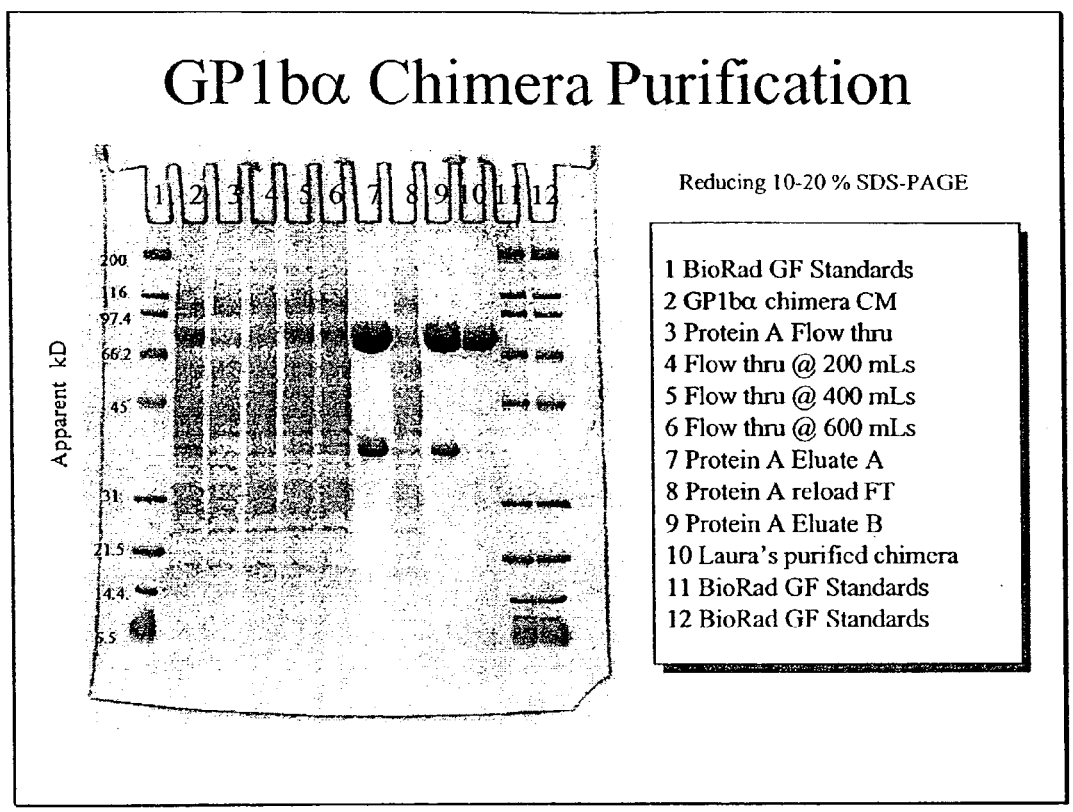
FIG. 1 is an illustration of a coomasie blue stained gel showing the purification of a GP1b302-Ig fusion protein secreted from CHO cells stably transfected with a mammalian expression vector containing a GP1b302-Ig coding region. Lanes 7,9 show protein A eluates containing tryptic fragments (lower band of approximately 38 kD). Lane 10 is protein A eluate after gel filtration column (GFC) as described in FIG. 2.
Figure 2:
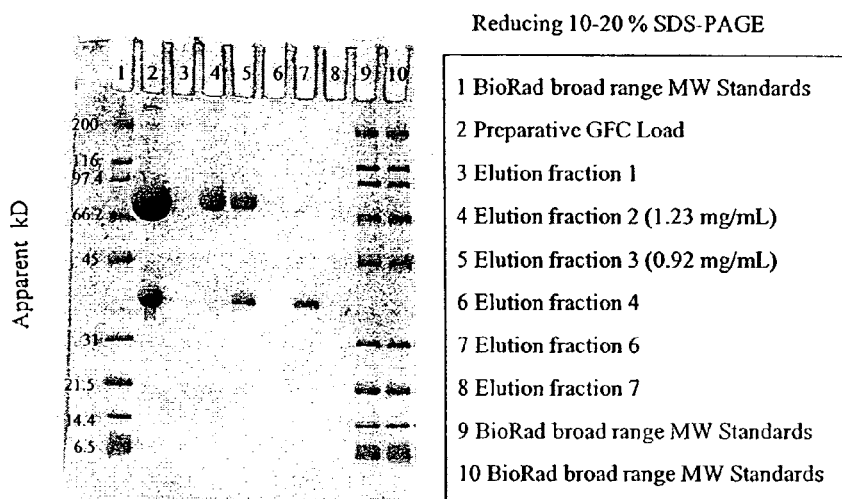
FIG. 2 is an illustration of a gel showing the purification of a protein A eluted GP1b302-Ig fusion protein by gel filtration column (GFC). GFC enables separation of upper band (intact fusion protein, lane 4) from lower band (tryptic cleavage fragment, lane 7).
Figure 3:
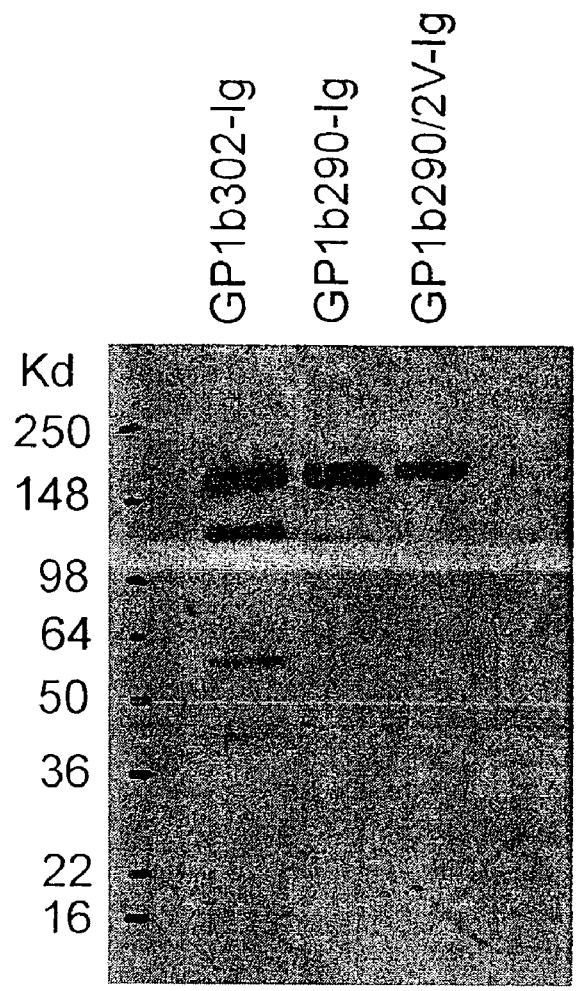
FIG. 3 is an illustration of a western blot of conditioned cell culture medium demonstrating the extent of proteolysis for various GP1b-Ig fusion proteins secreted from stability transfected CHO cells.

The invention provides fusion proteins containing glycoprotein Ibα protein-immunoglobulin fusion proteins that are useful for inhibiting adherence of platelets and leukocytes to biological tissues, such as for example the vascular endothelium. The fusion proteins of the invention, or nucleic acids encoding these fusion proteins, can be incorporated into pharmaceutical compositions and administered to a subject to inhibit an interaction between an glycoprotein Ibα ligand (such as Von Willebrand Factor, Mac-1, P-selectin or thrombin) and an glycoprotein Ibα protein on the surface of a cell, such as a platelet. Inhibition of binding suppresses glycoprotein Ibα protein-mediated platelet aggregation and associated signal transduction in vivo.

The glycoprotein Ibα protein-immunoglobulin fusion proteins can be used to modulate the bioavailability of a glycoprotein Ibα protein cognate ligand. Inhibition of the glycoprotein Ibα protein ligand/glycoprotein Ibα protein interaction are useful therapeutically for, inter alia, the treatment of vascular inflammation and other vascular disorders associated with platelet activation.

Glycoprotein Ibα Fusion Polypeptides

In various aspects the invention provides fusion proteins that include a first polypeptide containing at least a portion of a glycoprotein Ibα polypeptide operatively linked to a second polypeptide. As used herein, an glycoprotein Ibα "fusion protein" or "chimeric protein" includes at least a portion of a glycoprotein Ibα polypeptide operatively linked to a non-glycoprotein Ibα polypeptide. An "glycoprotein Ibα polypeptide" refers to a polypeptide having an amino acid sequence corresponding to at least a portion of a glycoprotein Ibα polypeptide, whereas a "non-glycoprotein Ibα polypeptide" refers to a polypeptide having an amino acid sequence corresponding to a protein that is not substantially homologous to the glycoprotein Ibα protein, e.g., a protein that is different from the glycoprotein Ibα polypeptide or fragment and that is derived from the same or a different organism. Within a glycoprotein Ibα fusion protein the glycoprotein Ibα polypeptide can correspond to all or a portion of an Ibα protein.

In one embodiment, a glycoprotein Ibα fusion protein comprises at least one biologically active portion of a glycoprotein Ibα protein. In another embodiment, a glycoprotein Ibα fusion protein comprises at least two biologically active portions of a glycoprotein Ibα protein. In yet another embodiment, a glycoprotein Ibα fusion protein comprises at least three biologically active portions of a glycoprotein Ibα protein. Within the fusion protein, the term "operatively linked" is intended to indicate that the first and second polypeptides are chemically linked (most typically via a covalent bond such as a peptide bond) in a manner that allows for at least one function associated with a glycoprotein Ibα polypeptide. When used to refer to nucleic acids encoding a glycoprotein Ibα fusion polypeptide, the term operatively linked means that a nucleic acid encoding the glycoprotein Ibα polypeptide and the non-glycoprotein Ibα polypeptide are fused in-frame to each other. The non-glycoprotein Ibα polypeptide can be fused to the N-termninus or C-terminus of the glycoprotein Ibα polypeptide.

In a further embodiment, the glycoprotein Ibα fusion protein may be linked to one or more additional moieties. For example, the glycoprotein Ibα fusion protein may additionally be linked to a GST fusion protein in which the glycoprotein Ibα fusion protein sequences are fused to the C-terminus of the GST (i.e., glutathione S-transferase) sequences. Such fusion proteins can facilitate the purification of glycoprotein Ibα fusion protein.

In another embodiment, the fusion protein is includes a heterologous signal sequence (i.e., a polypeptide sequence that is not present in a polypeptide encoded by a glycoprotein Ibα nucleic acid) at its N-terminus. For example, the native glycoprotein Ibα signal sequence can be removed and replaced with a signal sequence from another protein. In certain host cells (e.g., mammalian host cells), expression and/or secretion of glycoprotein Ibα can be increased through use of a heterologous signal sequence.

An chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A glycoprotein Ibα encoding nucleic acid can be cloned into such an expression vector such that the fusion moiety is linked in-frame to the immunoglobulin protein.

In various embodiments, the glycoprotein Ibα fusion polypeptide includes the amino acid sequence of one or more of SEQ ID NOs: 1–6.

Glycoprotein Ibα fusion polypeptides may exist as oligomers, such as dimers or trimers. Preferably the glycoprotein Ibα fusion polypeptide is a dimer.

The first polypeptide, and/or nucleic acids encoding the first polypeptide, can be constructed using GP Ibα encoding sequences are known in the art and are described in, e.g. European Patent Application Publication No. 0 317 278 A2, and Lopez et al. 84:5615–19, 1987. Other sources for GP Ibα polypeptides and nucleic acids encoding GP Ibα polypeptides include GenBank Accession Nos. BAB12038 and AB038516, D85894 and BAA12911, respectively (human sequences), and GenBank Accession No. AAC53320 and U91967, respectively, and are incorporated herein by reference in their entirety.

In some embodiments, the GP Ib α polypeptide moiety is provided as a variant GP Ib α polypeptide having a mutation in the naturally-occurring GP Ib α sequence (wild type) that results in higher affinity (relative to the non-mutated sequence) binding of the GP Iβα polypeptide to a leukocyte cell surface molecule. For example, the mutant polypeptide may bind with higher affinity to Von Willebrand factor (vWF). This increased reactivity, or hyperresponsiveness, can be assessed using low concentrations of ristocetin. Alternately, any other suitable means for determining the reactivity of the polypeptide with vWF can also be utilized to identify polypeptides which are "more" reactive with vWF, i.e. more reactive than naturally-occurring wild-type GP Ibα. Examples of GP Ib α polypeptide variants that bind with higher affinity to vWF include GP Ibα variants that include sequence alterations in the hinge region of a GP Ibα polypeptide. The hinge region is defined as the region including residues 220 to 310 and is reported to be a major binding site for vWF within the GP Ib α polypeptide. Mutations in the hinge region include those at residue 233, which in the wild-type GP Ib α encodes glycine. A substitution of valine for glycine 233 is preferred, but other amino acids could also be substituted. A second site for mutation at the hinge region is at residue 239, which in the wild-type GP Ib α encodes methionine. A substitution of valine for glycine 239 is preferred, but other amino acids can also be substituted. In addition, hinge region variants of GP Ib α polypeptides suitable for use in a fusion polypeptide of the invention have mutations oat residue both positions 233 and 239. (see e.g., Dong et al., JBC 275:36 27663–27670 (2000)) Thus, the invention includes fusion proteins that have a substitution at position 239, e.g., an M239V substititon of a variant GP Ib α polypeptide. Also within the invention is a fusion protein having a substitution at position 233, e.g., G233V, and a fusion protein that includes a a variant GP Ib α polypeptide with positions at both 233 and 239, e .g, a G233V and M239V substitution.

In some embodiments, the GP Ib α polypeptide moiety is provided as a variant GP Ib α polypeptide having mutations in the naturally-occurring GP Ib α sequence (wild type) that results in a GP Ib α sequence more resistant to proteolysis (relative to the non-mutated sequence). Tryptic cleavage sites in the naturally-occurring GP Ib α sequence have been described. (see e.g. Titani et al., PNAS 84: 5610–5614, (1987))

In some embodiments, the first polypeptide includes full-length GP Ib α polypeptide. Alternatively, the first polypeptide comprise less than full-length GP Ib α polypeptide. For example the first polypeptide less than 600 amino acids in length, e.g., less than or equal to 500, 250, 150, 100, 50, or 25 amino acids in length.

Examples of a first polypeptide include a polypeptide which includes the amino acid sequence of any of the GP Ib α polypeptide sequences of GP1b302 (SEQ ID NO:7), GP1b302/2A (SEQ ID NO:8) GP1b/4X (SEQ ID NO:9), GP1b290 (SEQ ID NO:10), GB1b290/2V (SEQ ID NO:11) and GB1b290/1A (SEQ ID NO:12).

HPICEVSKVASHLEVNCDKRNLTALPPDLPKDTTILHLSENLLYTFSLATLMPYTRLTQLNLDR (SEQ ID NO:7)
CELTKLQVDGTLPVLGTLDLSHNQLQSLPLLGQTLPALTVLDVSFNRLTSLPLGALRGLGELQE
LYLKGNELKTLPPGLLTPTPKLEKLSLANNNLTELPAGLLNGLENLDTLLLQENSLYTIPKGFF
GSHLLPFAFLHGNPWLCNCEILYFRRWLQDNAENVYVWKQGVDVKAMTSNVASVQCDNSDKFPV
YKYPGKGCPTLGDEGDTDLYDYYPEEDTEGDKVRATRTVVKFPTKA

HPICEVSKVASHLEVNCDKRNLTALPPDLPKDTTILHLSENLLYTFSLATLMPYTRLTQLNLDR (SEQ ID NO:8)
CELTKLQVDGTLPVLGTLDLSHNQLQSLPLLGQTLPALTVLDVSFNRLTSLPLGALRGLGELQE
LYLKGNELKTLPPGLLTPTPKLEKLSLANNNLTELPAGLLNGLENLDTLLLQENSLYTIPKGFF
GSHLLPFAFLHGNPWLCNCEILYFRRWLQDNAENVYVWKQGVDVKAMTSNVASVQCDNSDKFPV
YKYPGKGCPTLGDEGDTDLYDYYPEEDTEGDKVAATATVVKFPTKA

HPICEVSKVASHLEVNCDKRNLTALPPDLPKDTTILHLSENLLYTFSLATLMPYTRLTQLNLDR (SEQ ID NO:9)
CELTKLQVDGTLPVLGTLDLSHNQLQSLPLLGQTLPALTVLDVSFNRLTSLPLGALRGLGELQE
LYLKGNELKTLPPGLLTPTPKLEKLSLANNNLTELPAGLLNGLENLDTLLLQENSLYTIPKGFF
GSHLLPFAFLHGNPWLCNCEILYFRRWLQDNAENVYVWKQVVDVKAVTSNVASVQCDNSDKFPV
KYPGKGCPTLGDEGDTDLYDYYPEEDTEGDKVAATATVVKFPTKA

HPICEVSKVASHLEVNCDKRNLTALPPDLPKDTTILHLSENLLYTFSLATLMPYTRLTQLNLDR (SEQ ID NO:10)
CELTKLQVDGTLPVLGTLDLSHNQLQSLPLLGQTLPALTVLDVSFNRLTSLPLGALRGLGELQE
LYLKGNELKTLPPGLLTPTPKLEKLSLANNNLTELPAGLLNGLENLDTLLLQENSLYTIPKGFF
GSHLLPFAFLHGNPWLCNCEILYFRRWLQDNAENVYVWKQGVDVKAMTSNVASVQCDNSDKFPV
YKYPGKGCPTLGDEGDTDLYDYYPEEDTEGDKVR

HPICEVSKVASHLEVNCDKRNLTALPPDLPKDTTILHLSENLLYTFSLATLMPYTRLTQLNLDR (SEQ ID NO:11)
CELTKLQVDGTLPVLGTLDLSHNQLQSLPLLGQTLPALTVLDVSFNRLTSLPLGALRGLGELQE
LYLKGNELKTLPPGLLTPTPKLEKLSLANNNLTELPAGLLNGLENLDTLLLQENSLYTIPKGFF
GSHLLPFAFLHGNPWLCNCEILYFRRWLQDNAENVYVWKQVVDVKAVTSNVASVQCDNSDKFPV
YKYPGKGCPTLGDEGDTDLYDYYPEEDTEGDKVR

HPICEVSKVASHLEVNCDKRNLTALPPDLPKDTTILHLSENLLYTFSLATLMPYTRLTQLNLDR (SEQ ID NO:11)
CELTKLQVDGTLPVLGTLDLSHNQLQSLPLLGQTLPALTVLDVSFNRLTSLPLGALRGLGELQE
LYLKGNELKTLPPGLLTPTPKLEKLSLANNNLTELPAGLLNGLENLDTLLLQENSLYTIPKGFF
GSHLLPFAFLHGNPWLCNCEILYFRRWLQDNAENVYVWKQGVDVAAMTSNVASVQCDNSDKFPV
YKYPGKGCPTLGDEGDTDLYDYYPEEDTEGDKVR
YKYPGKGCPTLGDEGDTDLYDYYPEEDTEGDKVR
HPICEVSKVASHLEVNCDKRNLTALPPDLPKDTTILI-{LSENLLYTFSLATLMPYTRLTQLNLDR (SEQ ID NO: 12)
CELTKLQVDGTLPVLGTLDLSHNQLQs LPLLGQTLPALTVLDVS FNRLTSLPLGALRGLGELQE
LYLKGNELKTLPPGLLTPTPKLEKLSLANNNLTELPAGLLNGLENLDTLLLQENSLYTI PKGFF
GSHLLPFAFLHGNPWLCNCE I LYFRRWLQDNAENVYVWKQGVDVAANTSNVASVQCDNSDKFPv
YKYPGKGCPTLGDEGDTDLYIDYYPEEDTEGDKVR

A signal peptide that can be included in the fusion protein is MPLLLLLLLLPSPLHP (SEQ ID NO:13). If desired, one or more amino acids can additionally be inserted between the first polypeptide moiety comprising the GP Ib α moiety and the second polypeptide moiety.

The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second GP Ib α polypeptide. In preferred embodiments, the second polypeptide includes at least a region of an immunoglobulin polypeptide. Immunoglobulin fusion polypeptide are known in the art and are described in e.g., U.S. Pat. Nos. 5,516,964; 5,225,538; 5,428,130; 5,514,582; 5,714,147; and 5,455,165.

In some embodiments, the second polypeptide comprises a full-length immunoglobulin polypeptide. Alternatively, the second polypeptide comprise less than full-length immunoglobulin polypeptide, e.g., a heavy chain, light chain, Fab, Fab$_2$, Fv, or Fc. Preferably, the second polypeptide includes the heavy chain of an immunoglobulin polypeptide. More preferably the second polypeptide includes the Fc region of an immunoglobulin polypeptide.

In another aspect of the invention the second polypeptide has less effector function that the effector function of a Fc region of a wild-type immunoglobulin heavy chain. Fc effector function includes for example, Fc receptor binding, complement fixation and T cell depleting activity. (see for example, U.S. Pat. No. 6,136,310) Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

A preferred second polypeptide sequence includes the amino acid sequence of SEQ ID NO: 12. This sequence includes a Fc region. Underlined amino acids are those that differ from the amino acid found in the corresponding position of the wild-type immunoglobulin sequence:

```
HTCPPCPAPEALGAPSVFLFPPKPKDTLMISRTPEVTCVVDVSHEDPEVKFNWYVDGVEVHNAK    (SEQ ID NO:14)

TKPREEQYNSTYRVVSVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGSFFLYSKLTVDKSRWQ

QGNVFSCSVMHEALHNHYTQKSLSLSPGK
```

DNA sequences encoding fusion polypeptides of SEQ ID NOs:1–6 are disclosed below as sequences SEQ ID NOs; 15–20, respectively:

```
GP1b302-Ig nucleotide sequence atgcctctcctcctcttgctgctcctgctgccaagcccttacaccccacccatctgtgaggt    (SEQ ID NO:15)

ctccaaagtggccagccacctagaagtgaactgtgacaagaggaatctgacagcgctgcctccag acctgccgaaagacacaaccatcctccacctgagtgagaacctcctgtacaccttctccctggca accctgatgccttacactcgcctcactcagctgaacctagataggtgcgagctcaccaagctcca ggtcgatgggacgctgccagtgctggggaccctggatctatcccacaatcagctgcaaagcctgc ccttgctagggcagacactgcctgctctcaccgtcctggacgtctccttcaaccggctgacctcg ctgcctcttggtgccctgcgtggtcttggcgaactccaagagctctacctgaaaggcaatgagct gaagaccctgccccagggctcctgacgcccacacccaagctggagaagctcagtctggctaaca acaacttgactgagctccccgctgggctcctgaatgggctggagaatctcgacaccttctcctc caagagaactcgctgtatacaataccaaagggcttttttgggtcccacctcctgccttttgcttt tctccacgggaaccctggttatgcaactgtgagatcctctattttcgtcgctggctgcaggaca atgctgaaaatgtctacgtatggaagcaaggtgtggacgtcaaggccatgacctctaacgtggcc agtgtgcagtgtgacaattcagacaagtttcccgtctacaaatacccaggaaaggggtgccccac ccttggtgatgaaggtgacacagacctatatgattactacccagaagaggacactgagggcgata aggtcaagttcaactggtacgtggacggcgtggaggtgcataatgccaagacaaagccgcgggag tgcccagcacctgaagccctgggggcaccgtcagtcttcctcttcccccccaaaacccaaggacac cctcatgatctcccggaccctgaggtcacatgcgtggtggtggacgtgagccacgaagaccctg aggtcaagttcaactggtacgtggacggcgtggaggtgcataatgccaagacaaagccgcgggag
```

-continued gagcagtacaacagcacgtaccgtgtggtcagcgtcctcaccgtcctgcaccaggactggctgaa tggcaaggagtacaagtgcaaggtctccaacaaagccctcccagtccccatcgagaaaaccatct ccaaagccaaagggcagccccgagaaccacaggtgtacaccctgcccccatcccgggaggagatg accaagaaccaggtcagcctgacctgcctggtcaaaggcttctatcccagcgacatcgccgtgga gtgggagagcaatgggcagccggagaacaactacaagaccacgcctcccgtgctggactccgacg gcccttcttcctctacagcaagctcaccgtggacaagagcaggtggcagcaggggaacgtcttc tcatgctccgtgatgcatgaggctctgcacaaccactacacgcagaagagcctctccctgtctcc gggtaaa GP1b302/2a-Ig nucleotide sequence atgcctctcctcctcttgctgctcctgctgccaagcccttacaccccaccccatctgtgaggt (SEQ ID NO:16)

ctccaaagtggccagccacctagaagtgaactgtgacaagaggaatctgacagcgctgcctccag acctgccgaaagacacaaccatcctccacctgagtgagaacctcctgtacaccttctccctggca accctgatgccttacactcgcctcactcagctgaacctagataggtgcgagctcaccaagctcca ggtcgatgggacgctgccagtgctggggaccctggatctatcccacaatcagctgcaaagcctgc ccttgctagggcagacactgcctgctctcaccgtcctggacgtctccttcaaccggctgacctcg ctgcctcttggtgccctgcgtggtcttggcgaactccaagagctctacctgaaaggcaatgagct gaagaccctgcccccagggctcctgacgcccacacccaagctggagaagctcagtctggctaaca caacttgactgagctccccgctgggctcctgaatgggctggagaatctcgacacccttctcctc caagagaactcgctgtatacaataccaaagggcttttttgggtcccacctcctgccttttgcttt tctccacgggaaccctggttatgcaactgtgagatcctctattttcgtcgctggctgcaggaca atgctgaaaatgtctacgtatggaagcaaggtgtggacgtcaaggccatgacctctaacgtggcc agtgtgcagtgtgacaattcagacaagtttcccgtctacaaatacccaggaaagggggtgccccac ccttggtgatgaaggtgacacagacctatatgattactacccagaagaggacactgagggcgata aggtcaagttcaactggtacgtggacggcgtggaggtgcataatgccaagacaaagccgcgggag tgcccagcacctgaagccctggggcaccgtcagtcttcctcttccccccaaaacccaaggacac cctcatgatctcccggacccctgaggtcacatgcgtggtggtggacgtgagccacgaagaccctg aggtcaagttcaactggtacgtggacggcgtggaggtgcataatgccaagacaaagccgcgggag gagcagtacaacagcacgtaccgtgtggtcagcgtcctcaccgtcctgcaccaggactggctgaa tggcaaggagtacaagtgcaaggtctccaacaaagccctcccagtccccatcgagaaaaccatct ccaaagccaaagggcagccccgagaaccacaggtgtacaccctgcccccatcccgggaggagatg accaagaaccaggtcagcctgacctgcctggtcaaaggcttctatcccagcgacatcgccgtgga gtgggagagcaatgggcagccggagaacaactacaagaccacgcctcccgtgctggactccgacg gcccttcttcctctacagcaagctcaccgtggacaagagcaggtggcagcaggggaacgtcttc tcatgctccgtgatgcatgaggctctgcacaaccactacacgcagaagagcctctccctgtctcc gggtaaa GP1b302/4X-Ignucleotide sequence atgcctctcctcctcttgctgctcctgctgccaagcccttacaccccaccccatctgtgaggt (SEQ ID NO:17)

ctccaaagtggccagccacctagaagtgaactgtgacaagaggaatctgacagcgctgcctccag acctgccgaaagacacaaccatcctccacctgagtgagaacctcctgtacaccttctccctggca accctgatgccttacactcgcctcactcagctgaacctagataggtgcgagctcaccaagctcca -continued

```
ggtcgatgggacgctgccagtgctggggaccctggatctatcccacaatcagctgcaaagcctgc ccttgctagggcagacactgcctgctctcaccgtcctggacgtctccttcaaccggctgacctcg ctgcctcttggtgccctgcgtggtcttggcgaactccaagagctctacctgaaaggcaatgagct gaagaccctgccccagggctcctgacgcccacacccaagctggagaagctcagtctggctaaca acaacttgactgagctccccgctgggctcctgaatgggctggagaatctcgacaccttctcctc caagagaactcgctgtatacaataccaaagggctttttggtcccacctcctgccttttgcttt tctccacgggaaccctggttatgcaactgtgagatcctctattttcgtcgctggctgcaggaca atgctgaaaatgtctacgtatggaagcaaggtgtggacgtcaaggccatgacctctaacgtggcc agtgtgcagtgtgacaattcagacaagtttcccgtctacaaatacccaggaaaggggtgccccac ccttggtgatgaaggtgacacagacctatatgattactacccagaagaggacactgagggcgata aggtcaagttcaactggtacgtggacggcgtggaggtgcataatgccaagacaaagccgcgggag tgcccagcacctgaagccctggggcaccgtcagtcttcctcttccccccaaaacccaaggacac cctcatgatctcccggacccctgaggtcacatgcgtggtggtggacgtgagccacgaagaccctg aggtcaagttcaactggtacgtggacggcgtggaggtgcataatgccaagacaaagccgcgggag gagcagtacaacagcacgtaccgtgtggtcagcgtcctcaccgtcctgcaccaggactggctgaa tggcaaggagtacaagtgcaaggtctccaacaaagcccteccagtccccatcgagaaaaccatct ccaaagccaaagggcagccccgagaaccacaggtgtacaccctgcccccatcccgggaggagatg accaagaaccaggtcagcctgacctgcctggtcaaaggcttctatcccagcgacatcgccgtgga gtgggagagcaatgggcagccggagaacaactacaagaccacgcctcccgtgctggactccgacg gccccttcttcctctacagcaagctcaccgtggacaagagcaggtggcagcaggggaacgtcttc tcatgctccgtgatgcatgaggctctgcacaaccactacacgcagaagagcctctccctgtctcc gggtaaa
```

GP1b290-Ig nucleotide sequence

```
atgcctctcctcctcttgctgctcctgctgccaagcccttacaccccaccccatctgtgaggt     (SEQ ID NO:18)

ctccaaagtggccagccacctagaagtgaactgtgacaagaggaatctgacagcgctgcctccag acctgccgaaagacacaaccatcctccacctgagtgagaacctcctgtacaccttctccctggca accctgatgccttacactcgcctcactcagctgaacctagataggtgcgagctcaccaagctcca ggtcgatgggacgctgccagtgctggggaccctggatctatcccacaatcagctgcaaagcctgc ccttgctagggcagacactgcctgctctcaccgtcctggacgtctccttcaaccggctgacctcg ctgcctcttggtgccctgcgtggtcttggcgaactccaagagctctacctgaaaggcaatgagct gaagaccctgccccagggctcctgacgcccacacccaagctggagaagctcagtctggctaaca acaacttgactgagctccccgctgggctcctgaatgggctggagaatctcgacaccttctcctc caagagaactcgctgtatacaataccaaagggctttttggtcccacctcctgccttttgcttt tctccacgggaaccctggttatgcaactgtgagatcctctattttcgtcgctggctgcaggaca atgctgaaaatgtctacgtatggaagcaaggtgtggacgtcaaggccatgacctctaacgtggcc agtgtgcagtgtgacaattcagacaagtttcccgtctacaaatacccaggaaaggggtgccccac ccttggtgatgaaggtgacacagacctatatgattactacccagaagaggacactgagggcgata aggtcaagttcaactggtacgtggacggcgtggaggtgcataatgccaagacaaagccgcgggag ctcttccccccaaaacccaaggacaccctcatgatctcccggacccctgaggtcacatgcgtggt ggtggacgtgagccacgaagaccctgaggtcaagttcaactggtacgtggacggcgtggaggtgc
```

-continued ataatgccaagacaaagccgcgggaggagcagtacaacagcacgtaccgtgtggtcagcgtcctc accgtcctgcaccaggactggctgaatggcaaggagtacaagtgcaaggtctccaacaaagccct cccagtccccatcgagaaaaccatctccaaagccaaagggcagccccgagaaccacaggtgtaca ttctatcccagcgacatcgccgtggagtgggagagcaatgggcagccggagaacaactacaagac cacgcctcccgtgctggactccgacggccccttcttcctctacagcaagctcaccgtggacaaga gcaggtggcagcaggggaacgtcttctcatgctccgtgatgcatgaggctctgcacaaccactac acgcagaagagcctctccctgtctccgggtaaa GP1b290/2V-Ig nucleotide sequence atgcctctcctcctcttgctgctcctgctgccaagcccttacaccccacccatctgtgaggt (SEQ ID NO:19)

ctccaaagtggccagccacctagaagtgaactgtgacaagaggaatctgacagcgctgcctccag acctgccgaaagacacaaccatcctccacctgagtgagaacctcctgtacaccttctccctggca accctgatgccttacactcgcctcactcagctgaacctagataggtgcgagctcaccaagctcca ggtcgatgggacgctgccagtgctggggaccctggatctatcccacaatcagctgcaaagcctgc ccttgctagggcagacactgcctgctctcaccgtcctggacgtctccttcaaccggctgacctcg ctgcctcttggtgccctgcgtggtcttggcgaactccaagagctctacctgaaaggcaatgagct gaagaccctgccccagggctcctgacgcccacacccaagctggagaagctcagtctggctaaca caacttgactgagctccccgctgggctcctgaatgggctggagaatctcgacacccttctcctc caagagaactcgctgtatacaataccaaagggcttttttgggtcccacctcctgccttttgcttt tctccacgggaaccctggttatgcaactgtgagatcctctattttcgtcgctggctgcaggaca atgctgaaaatgtctacgtatggaagcaaggtgtggacgtcaaggccatgacctctaacgtggcc agtgtgcagtgtgacaattcagacaagtttcccgtctacaaatacccaggaaaggggtgccccac ccttggtgatgaaggtgacacagacctatatgattactacccagaagaggacactgagggcgata aggtcaagttcaactggtacgtggacggcgtggaggtgcataatgccaagacaaagccgcgggag ctcttccccaaaaacccaaggacaccctcatgatctcccggacccctgaggtcacatgcgtggt ggtggacgtgagccacgaagaccctgaggtcaagttcaactggtacgtggacggcgtggaggtgc ataatgccaagacaaagccgcgggaggagcagtacaacagcacgtaccgtgtggtcagcgtcctc accgtcctgcaccaggactggctgaatggcaaggagtacaagtgcaaggtctccaacaaagccct cccagtccccatcgagaaaaccatctccaaagccaaagggcagccccgagaaccacaggtgtaca ccctgccccatcccgggaggagatgaccaagaaccaggtcagcctgacctgcctggtcaaaggc ttctatcccagcgacatcgccgtggagtgggagagcaatgggcagccggagaacaactacaagac cacgcctcccgtgctggactccgacggccccttcttcctctacagcaagctcaccgtggacaaga gcaggtggcagcaggggaacgtcttctcatgctccgtgatgcatgaggctctgcacaaccactac acgcagaagagcctctccctgtctccgggtaaa GP1b290/1A-Ig nucleotide sequence atgcctctcctcctcttgctgctcctgctgccaagcccttacaccccacccatctgtgaggt (SEQ ID NO:20)

ctccaaagtggccagccacctagaagtgaactgtgacaagaggaatctgacagcgctgcctccag acctgccgaaagacacaaccatcctccacctgagtgagaacctcctgtacaccttctccctggca accctgatgccttacactcgcctcactcagctgaacctagataggtgcgagctcaccaagctcca ggtcgatgggacgctgccagtgctggggaccctggatctatcccacaatcagctgcaaagcctgc ccttgctagggcagacactgcctgctctcaccgtcctggacgtctccttcaaccggctgacctcg -continued
```
ctgcctcttggtgccctgcgtggtcttggcgaactccaagagctctacctgaaaggcaatgagct gaagaccctgccccagggctcctgacgcccacacccaagctggagaagctcagtctggctaaca acaacttgactgagctcccgctgggctcctgaatgggctggagaatctcgacaccttctcctc caagagaactcgctgtatacaataccaaagggcttttttgggtcccacctcctgcttttgcttt tctccacgggaaccctggttatgcaactgtgagatcctctattttcgtcgctggctgcaggaca atgctgaaaatgtctacgtatggaagcaaggtgtggacgtcaaggccatgacctctaacgtggcc agtgtgcagtgtgacaattcagacaagtttcccgtctacaaatacccaggaaaggggtgcccac ccttggtgatgaaggtgacacagacctatatgattactacccagaagaggacactgagggcgata aggtcaagttcaactggtacgtggacggcgtggaggtgcataatgccaagacaaagccgcgggag ctcttcccccaaaaacccaaggacaccctcatgatctcccggacccctgaggtcacatgcgtggt ggtggacgtgagccacgaagaccctgaggtcaagttcaactggtacgtggacggcgtggaggtgc ataatgccaagacaaagccgcgggaggagcagtacaacagcacgtaccgtgtggtcagcgtcctc accgtcctgcaccaggactggctgaatggcaaggagtacaagtgcaaggtctccaacaaagccct cccagtccccatcgagaaaaccatctccaaagccaaagggcagccccgagaaccacaggtgtaca ccctgcccccatcccgggaggagatgaccaagaaccaggtcagcctgacctgcctggtcaaaggc ttctatcccagcgacatcgccgtggagtgggagagcaatgggcagccggagaacaactacaagac cacgcctcccgtgctggactccgacggcccctccttcctctacagcaagctcaccgtggacaaga gcaggtggcagcaggggaacgtcttctcatgctccgtgatgcatgaggctctgcacaaccactac acgcagaagagcctctccctgtctccgggtaaa
```

Another aspect of the invention pertains to vectors, preferably expression vectors, containing a nucleic acid encoding glycoprotein Ibα fusion polypeptides, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., glycoprotein Ibα fusion polypeptides, mutant forms of glycoprotein Ibα fusion polypeptides, etc.).

The recombinant expression vectors of the invention can be designed for expression of glycoprotein Ibα fusion polypeptides in prokaryotic or eukaryotic cells. For example, glycoprotein Ibα fusion polypeptides can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the glycoprotein Ibα fusion polypeptide expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, glycoprotein Ibα fusion polypeptide can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, el al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOV glycoprotein Ibα fusion polypeptide mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, glycoprotein Ibα fusion polypeptides can be expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding glycoprotein Ibα fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) glycoprotein Ibα fusion polypeptides. Accordingly, the invention further provides methods for producing glycoprotein Ibα fusion polypeptides using the host cells of the invention. In one embodiment, the method comprises culturing the host cell of invention (into which a recombinant expression vector encoding glycoprotein Ibα fusion polypeptides has been introduced) in a suitable medium such that glycoprotein Ibα fusion polypeptides is produced. In another embodiment, the method further comprises isolating glycoprotein Ibα fusion polypeptide from the medium or the host cell.

The fusion polypeptides may be isolated and purified in accordance with conventional conditions, such as extraction, precipitation, chromatography, affinity chromatography, electrophoresis or the like. For example, the immunoglobulin fusion proteins may be purified by passing a solution through a column which contains immobilized protein A or protein G which selectively binds the Fc portion of the fusion protein. See, for example, Reis, K. J., et al., J. Immunol. 132:3098–3102 (1984); PCT Application, Publication No. WO87/00329. The fusion polypeptide may be be eluted by treatment with a chaotropic salt or by elution with aqueous acetic acid (1 M).

Alternatively, fusion polypeptides according to the invention can be chemically synthesized using methods known in the art. Chemical synthesis of polypeptides is described in, e.g., A variety of protein synthesis methods are common in the art, including synthesis using a peptide synthesizer. See, e.g., *Peptide Chemistry, A Practical Textbook*, Bodasnsky, Ed. Springer-Verlag, 1988; Merrifield, *Science* 232: 241–247 (1986); Barany, et al, *Intl. J. Peptide Protein Res.* 30: 705–739 (1987); Kent, *Ann. Rev. Biochem.* 57:957–989 (1988), and Kaiser, et al, *Science* 243: 187–198 (1989). The polypeptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of polypeptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. *J. Med. Chem.* 36: 2585–2594; Kirby, et al., 1993. *J. Med. Chem.* 36:3802–3808; Morita, et al., 1994. *FEBS Lett*. 353: 84–88; Wang, et al., 1993. *Int. J. Pept. Protein Res.* 42: 392–399; Fauchere and Thiunieau, 1992. *Adv. Drug Res*. 23: 127–159.

Introduction of covalent cross-links into a peptide sequence can conformationally and topographically constrain the polypeptide backbone. This strategy can be used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137: 5182–5185 (1996)), or between two amino acid side chains. See, e.g., DeGrado, *Adv Protein Chem*, 39: 51–124 (1988). Disulfide bridges are also introduced into linear sequences to reduce their flexibility. See, e.g., Rose, et al., *Adv Protein Chem*, 37: 1–109 (1985); Mosberg et al., *Biochem Biophys Res Commun*, 106: 505–512 (1982). Furthermore, the replacement of cysteine residues with penicillamine (Pen, 3-mercapto-(D) valine) has been used to increase the selectivity of some opioid-receptor interactions. Lipkowski and Carr, *Peptides: Synthesis, Structures, and Applications*, Gutte, ed., Academic Press pp. 287–320 (1995).

Pharmaceutical Compositions Including Glycoprotein Ibα Fusion Polypeptides or Nucleic Acids Encoding Same The glycoprotein Ibα fusion proteins, or nucleic acid molecules encoding these fusion proteins, (also referred to herein as "Therapeutics" or "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e g., a glycoprotein Ibα fusion protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Methods of Inhibiting Adherence of in a Biological System

Also included in the invention are methods of inhibiting adherence of a blood cell to a biological tissue in a biological system. The method includes adding to a biological system a fusion polypeptide of the invention in an amount sufficient to inhibit adherence of a blood cell to the biological tissue.

The blood cell can be for example, a leukocyte, platelet or red blood cell. The leukocyte can be any leukocyte that is capable of adhering to a biological tissue. In various aspects the leukocyte is a granulocyte, (i.e., neutrophil, basophil or eosinohil), monocyte (i.e., macrophage) or lymphocyte (e.g., T-lymphocyte, B-lymphocyte, tumor infiltrating lymphocytes or natural killer cell). In some embodiments, the leukocytes express a β2 intergin, e.g. Mac-1. Alternately, the leuckocyte expresses a selectin ligand.

Also included in the inventions are methods of inhibiting adherence of a protein to a biological tissue in a biological system. The method includes adding to a biological system a fusion polypeptide of the invention in an amount sufficient to inhibit adherence of the protein to the biological tissue.

The protein can be membrane associated (e.g., covalently, non-covalently, ionicly). Alternatively, the protein can be in a soluble form (i.e., in solution). The protein is von Willibrand Factor, thrombin, P-selectin of glycoprotein Ibα.

As used herein a "biological tissue" is meant to include one or more cells with or without intracellular substances (e.g., extracellular matrix proteins, polysaccharides and proteoglycans. A biological tissue also includes solely extracellular matrix substances, such as the subendothelium connective tissue matrix. In some aspects the biological tissue is the vascular endothelium. The biological tissue can be one or more platelets or leukocytes. In various aspects the biological tissue is complexed with a component of the GP Ib-IX-V complex such as glycoprotein Ib α, Mac-1, P-selectin, thrombin or a von Willibrand Factor. By "complexed" is meant that the biological tissue contains a soluble form of a component of the GP Ib-IX-V complex. Alternatively, "complexed" is meant that the biological tissue contains a cell that expresses a component of the GP Ib-IX-V complex.

As used herein a biological system is meant to include any system that comprises biological components, e.g., cells, proteins, carbohydrates, lipids or nucleic acids. The biological system can be an in vivo, ex vivo or in vitro system.

By "adherence" is meant to include any leukocyte-biological interaction, e.g., rolling, firm attachments or specific interaction.

Inhibition of adherence of a blood cell or protein to a biological tissue can be measured using methods known in the art. For example, assays for detecting binding of glycoprotein Ibα to a biological tissue are described in Simon et al., J. Exp. Med. 192:193–204, 2000, and references cited therein. In various embodiments, binding of a GP Ib α fusion protein inhibits binding of a blood cell or protein to a biological tissue by at least 30%, 50%, 75%, 90%, 95%, 99% or 99.9%.

Adherence can also be assessed in condition of greater or less than physiological flow conditions, including static conditions and serial application of static and shear conditions. Adherence can be determined for example colormetrically, flourometrically, by flow cytometry or using a parrallel plate flow chamber assay.

Also included in the invention are methods of treating platelet activation associated disorders in a subject by administering to a subject a biologically-active therapeutic compound (hereinafter "Therapeutic"). Alternatively, the subject is also administered one or more of the following acetylsalicylic acid, e.g., aspirin heparin, e.g., unfractionated or low-molecular weight heparins, glycoprotein IIb/IIIa antagonists, clopidogrel, P-selectin antagonists, thrombin inhibitors or thrombolytic enzymes.

The subject can be e.g., any mammal, e.g., a human, a primate, mouse, rat, dog, cat, cow, horse, pig.

The Therapeutics include, e.g.: (i) any one or more of the glycoprotein Ibα fusion polypeptides, and derivative, fragments, analogs and homologs thereof, (ii) antibodies directed against the glycoprotein Ibα fusion polypeptides; and (iii) nucleic acids encoding a glycoprotein Ibα fusion polypeptide, and derivatives, fragments, analogs and homologs thereof.

Essentially, any disorder, which is etiologically linked to platelet activation, is considered amenable to prevention or to treatment. The disorder can be, e.g., vascular inflammation, atherosclerosis, restenosis (e.g., angioplasty-related restenosis) and/or a condition associated with thrombotic disease, e.g., angina, (i.e., stable angina and unstable angia) acute myocardial infarction, stoke, venous thrombosis or arterial thrombosis.

The invention will be further illustrated in the following non-limiting examples.

EXAMPLE 1

Production and Purification of Recombinant GP1B-IG Fusion Proteins

Three GP1b-Ig fusion proteins, GP1b302-Ig (SEQ ID NO:1), GP1b290 Ig (SEQ ID NO:4), and GP1b290/2V-Ig (SEQ ID NO:5), were produced by recombinant methods and purified. Chinese hamster ovary (CHO) cells lacking dihydrofolate reductase (DHFR) activity were stability transfected with linearized plasmid DNA consisting of a mammalian expression vector directing the transcription of a GP1b-Ig coding regions in polycistronic fashion with a DHFR selectable maker gene. Candidate expressing cells were selected in medium containing increasing concentrations of methotrexate (MTX) essentially as described in Kaufmnan et al. *Nucleic Acids Res.* (1991)19:4485–90. For collection of GP1b-Ig conditioned medium, CHO cells were grown to near confluent levels on 5–20 culture dishes (150 mm diameter), the cell monolayer was washed twice with PBS and cells were cultured for approximately 24 hrs in medium lacking fetal bovine serum. The medium was then collected and cells discarded.

CHO cell condition media (CM) was adjusted to 50 mM Tris pH8.0, 200 mM NaCl, filtered through a 0.2 um filter, and applied to a Poros Protein A column. The column was washed with 10 column volumes of 50 mM Tris pH8.0, 200 mM NaCl and eluted with Pierce IgG elution buffer. The protein peak was followed by absorbance at 280 nM. The pH of the elute was adjusted with 0.1 volumes of 1 M Tris, pH 8.0. The protein was then concentrated and the buffer exchanged by finger dialysis (25 kD MWCO) against TBS (10 mM Tris, pH 8.0, 150 mM NaCl). The concentrated protein was then further purified by gel filtration chromatography on a TosoHaas G3000SW column run in TBS.

The purified protein was analyzed by Western Blots. Briefly, 13 microliters of CHO cell conditioned medium was loaded per lane on a 4–20% reducing SDS PAGE gel. Western transfer was performed using Electroblot apparatus and nitrocellulose membrane (Novex, San Diego, Calif.). The primary detection antibody was monoclonal AP1, and secondary antibody was an HRP-conjugated goat anti-murine IgG (GTI, Brookfield, Wis.). HRP detection was via ECL system (Amersham-Pharmacia Biotech).

EXAMPLE 2

In Vitro Inhibition of Platelet Aggregation

Figure 4:
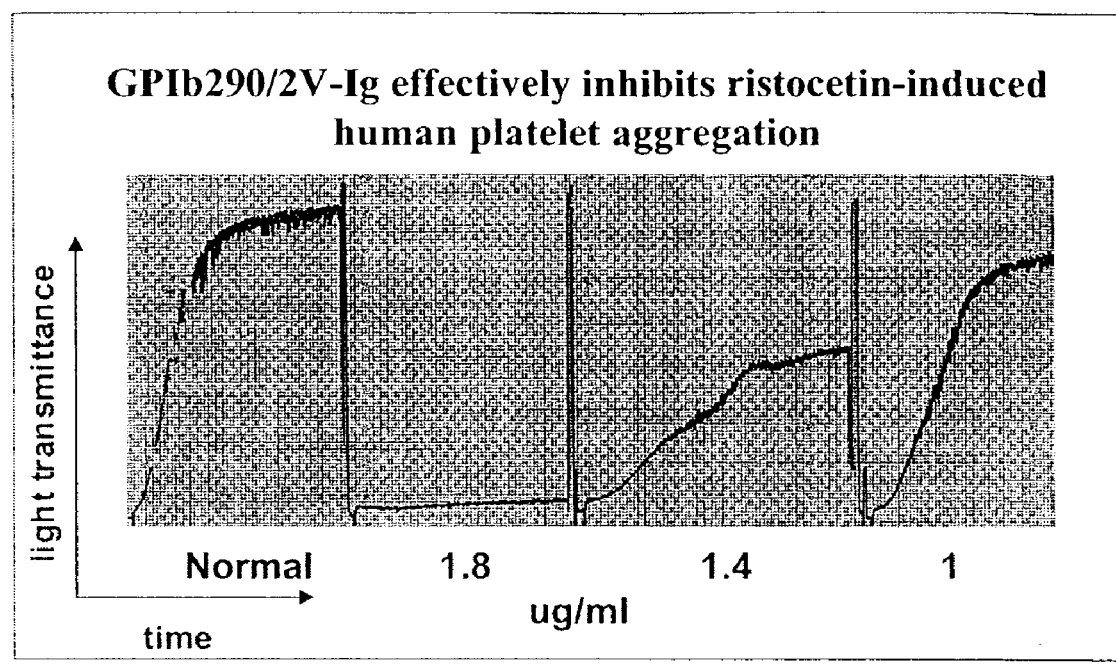
FIG. 4 is a chart depicting an UV spectrum measuring platelet aggregation.

The ability of the glycoprotein Ibα polypeptide-immunoglobulin fusion polypeptide to inhibit platelet aggregation in vitro, was determined. Platelet rich plasma (PRP) from freshly drawn, citrate blood was prepared by differential centrifugation for 10 minutes at 900 rpm. 0.4 mls of PRP ($3 \times 10^8$/ml) was preincubated for 5 minutes at 37° C. with various concentrations of GP1b290/2v-Ig. Ristocetin was added to 1.5 mg/ml to induce platelet aggregation. Aggregation was measured using a Sienco DP247E aggregometer. Aggregation was quantified and recorded on a chart recorder by monitoring the increase in light transmittance with stirring at 1000 rpm. As illustrated in FIG. 4, GP1b290/2v-Ig inhibited ristocetin induced platelet aggregation.

EXAMPLE 3

In Vivo Inhibition of Repetitive Coronary Artery Thrombosis

The ability of a glycoprotein Ibα GPIb290/2V-Ig polypeptide-immunoglobulin fusion polypeptide to inhibit coronary artery thrombosis in vivo was determined using the procedure described by Folts at al., Circulation 54:365–70, 1976.

Mongrel dogs, weighing 20–25 kg, were anesthetized with sodium pentobarbital (30 mg/kg i.v.), then intubated and ventilated with room air using a respirator. Venous and arterial cathetors were placed. The heart was approached by left thoracotomy through the fifth intercostal space. The pericardium was opened and sutured to the wound edges to provide a cradle without displacing the heart. About 2 cm of the left circumflex coronary artery (LCX) was isolated. Mean and dynamic LCX flow was continuously monitored using a perivascular ultrasonic flow probe placed proximally on the artery. After a stabilization period, the endothelium of the LCX was injured by squeezing with a hemostat. A plastic constrictor was placed distal and overlying the area of injured endothelium to provide approximately 70–80% vessel stenosis. When blood flow decreased to zero, the blood flow was restored by shaking the constrictor to dislodge aggregated platelets. This decrease and restoration of blood flow are termed CFRs. At least five consecutive CFRs were recorded prior to administering the test drug.

Figure 5:
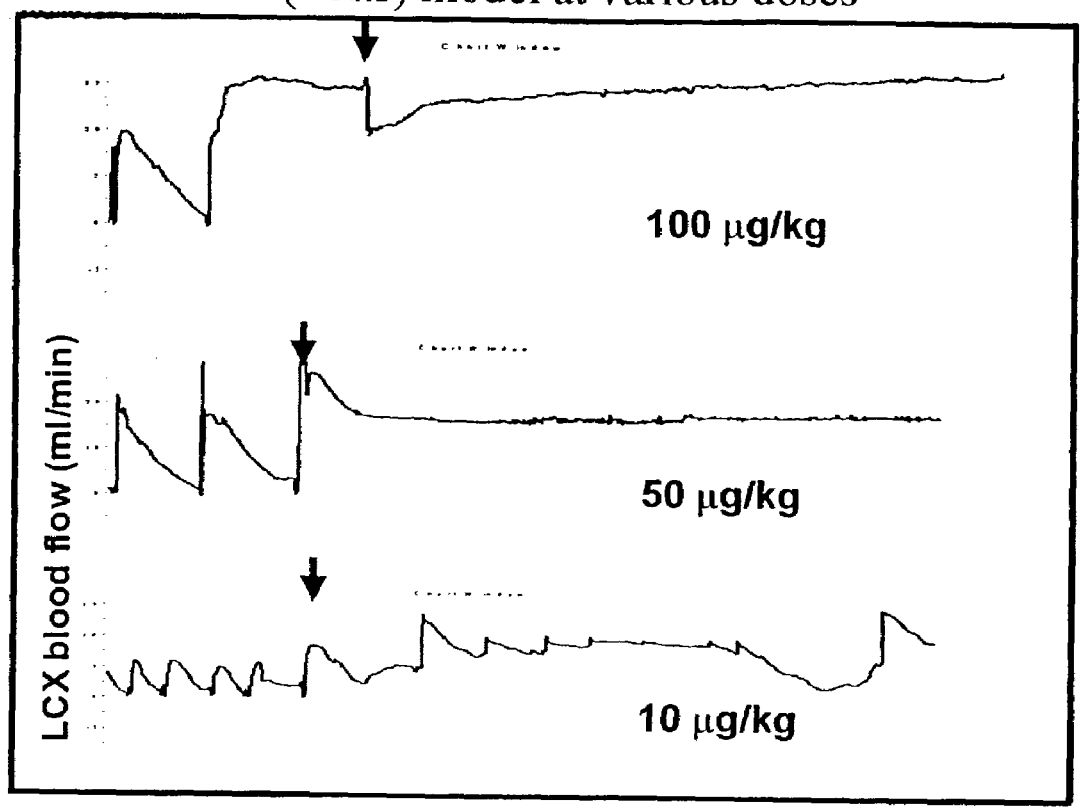
FIG. 5 is a chart showing the effect of a single bolus injection of a GP1b290/2V-Ig fusion protein at various concentrations on mean LCX flow patterns during in vivo Folts model experiments. Arrow shows time of drug injection.

Representative results are shown in FIG. 5. The tracings indicate that increasing amounts of of glycoprotein Ibα GPIb290/2V-Ig resulted in higher blood flow. These results demonstrate that glycoprotein Ibα GPIb290/2V-Ig inhibits thrombosis in the animal model.

Figure 6:
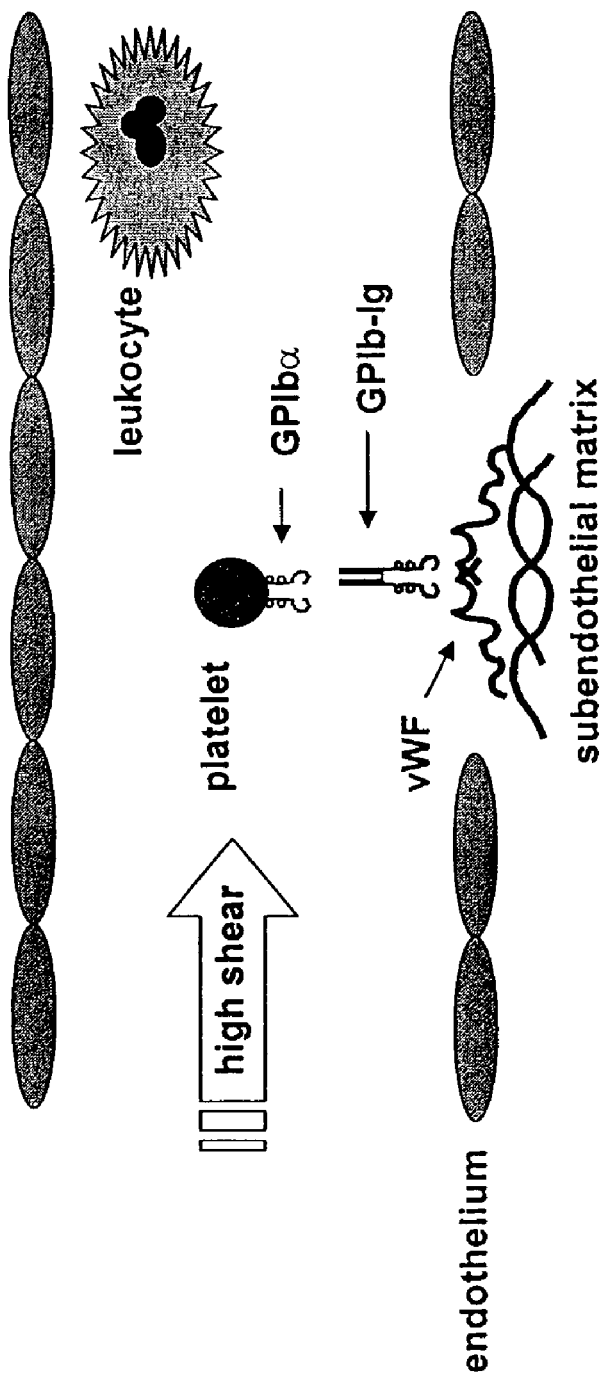
FIG. 6 is a schematic illustration depicting an injured coronary artery with high fluid shear blood flow.

A schematic illustration depicting an injured coronary artery with high fluid shear blood flow is presented in FIG. 6. The figure depicts an injured coronary arterty with high fluid shear blood flow. The vessel has a segment of damaged endothelium that exposes subendothelial matrix proteins, including immobilized vWF. In the presence of GP1b alpha fusion polypeptide (GPIb-Ig), the vWF binding site is blocked, thereby preventing platelet adherence via the platelet-bound GPIb alpha within the GPIb-V-IX complex. Lukocyte capture is also diminished.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule encoding a glycoprotein Ibα polypeptide-immunoglobulin fusion polypeptide comprising the amino acid sequence of SEQ ID NO:5.

2. A vector comprising the nucleic acid molecule of claim 1.

3. An isolated cell comprising the vector of claim 2.

4. A method for expressing glycoprotein Ibα polypeptide-immunoglobulin fusion polypeptide comprising the amino acid sequence of SEQ ID NO:5, the method comprising culturing the cell of claim 3 under conditions that result in expression of said fusion polypeptide.

5. A composition comprising the nucleic acid of claim 1.

6. The nucleic acid molecule of claim 1, wherein the amino acid sequence of the polypeptide consists of SEQ ID NO:5.

7. A nucleic acid molecule encoding a multimeric polypeptide comprising the polypeptide encoded by the nucleic acid of claim 1.

8. The nucleic acid molecule of claim 7, wherein said multimeric polypeptide is a dimer.

* * * * *

```
                              SEQUENCE LISTING

<160> NUMBER OF SEQ ID NOS: 20

<210> SEQ ID NO 1
<211> LENGTH: 544
<212> TYPE: PRT
<213> ORGANISM: Homo sapiens
<220> FEATURE:
<221> NAME/KEY: DOMAIN
<222> LOCATION: (1)..(544)
<223> OTHER INFORMATION: GP1b302-Ig

<400> SEQUENCE: 1

Met Pro Leu Leu Leu Leu Leu Leu Leu Pro Ser Pro Leu His Pro
  1               5                  10                  15

His Pro Ile Cys Glu Val Ser Lys Val Ala Ser His Leu Glu Val Asn
                 20                  25                  30

Cys Asp Lys Arg Asn Leu Thr Ala Leu Pro Pro Asp Leu Pro Lys Asp
             35                  40                  45

Thr Thr Ile Leu His Leu Ser Glu Asn Leu Leu Tyr Thr Phe Ser Leu
         50                  55                  60

Ala Thr Leu Met Pro Tyr Thr Arg Leu Thr Gln Leu Asn Leu Asp Arg
 65                  70                  75                  80

Cys Glu Leu Thr Lys Leu Gln Val Asp Gly Thr Leu Pro Val Leu Gly
                 85                  90                  95

Thr Leu Asp Leu Ser His Asn Gln Leu Gln Ser Leu Pro Leu Leu Gly
                100                 105                 110

Gln Thr Leu Pro Ala Leu Thr Val Leu Asp Val Ser Phe Asn Arg Leu
            115                 120                 125

Thr Ser Leu Pro Leu Gly Ala Leu Arg Gly Leu Gly Glu Leu Gln Glu
    130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175

Thr Glu Leu Pro Ala Gly Leu Leu Asn Gly Leu Glu Asn Leu Asp Thr
            180                 185                 190

Leu Leu Leu Gln Glu Asn Ser Leu Tyr Thr Ile Pro Lys Gly Phe Phe
        195                 200                 205

Gly Ser His Leu Leu Pro Phe Ala Phe Leu His Gly Asn Pro Trp Leu
    210                 215                 220

Cys Asn Cys Glu Ile Leu Tyr Phe Arg Arg Trp Leu Gln Asp Asn Ala
225                 230                 235                 240

Glu Asn Val Tyr Val Trp Lys Gln Gly Val Asp Val Lys Ala Met Thr
                245                 250                 255

Ser Asn Val Ala Ser Val Gln Cys Asp Asn Ser Asp Lys Phe Pro Val
            260                 265                 270

Tyr Lys Tyr Pro Gly Lys Gly Cys Pro Thr Leu Gly Asp Glu Gly Asp
        275                 280                 285

Thr Asp Leu Tyr Asp Tyr Pro Glu Glu Asp Thr Glu Gly Asp Lys
    290                 295                 300

Val Arg Ala Thr Arg Thr Val Val Lys Phe Pro Thr Lys Ala Arg Pro
305                 310                 315                 320
```

```
His Thr Cys Pro Pro Cys Pro Ala Pro Glu Ala Leu Gly Ala Pro Ser
                325                 330                 335

Val Phe Leu Phe Pro Lys Pro Lys Asp Thr Leu Met Ile Ser Arg
                340                 345                 350

Thr Pro Glu Val Thr Cys Val Val Val Asp Val Ser His Glu Asp Pro
                355                 360                 365

Glu Val Lys Phe Asn Trp Tyr Val Asp Gly Val Glu Val His Asn Ala
        370                 375                 380

Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
                405                 410                 415

Lys Cys Lys Val Ser Asn Lys Ala Leu Pro Val Pro Ile Glu Lys Thr
                420                 425                 430

Ile Ser Lys Ala Lys Gly Gln Pro Arg Glu Pro Gln Val Tyr Thr Leu
                435                 440                 445

Pro Pro Ser Arg Glu Glu Met Thr Lys Asn Gln Val Ser Leu Thr Cys
450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
                500                 505                 510

Arg Trp Gln Gln Gly Asn Val Phe Ser Cys Ser Val Met His Glu Ala
                515                 520                 525

Leu His Asn His Tyr Thr Gln Lys Ser Leu Ser Leu Ser Pro Gly Lys
                530                 535                 540

<210> SEQ ID NO 2
<211> LENGTH: 544
<212> TYPE: PRT
<213> ORGANISM: Homo sapiens
<220> FEATURE:
<221> NAME/KEY: DOMAIN
<222> LOCATION: (1)..(544)
<223> OTHER INFORMATION: GP1b302/2A-Ig

<400> SEQUENCE: 2

Met Pro Leu Leu Leu Leu Leu Leu Leu Pro Ser Pro Leu His Pro
  1               5                  10                 15

His Pro Ile Cys Glu Val Ser Lys Val Ala Ser His Leu Glu Val Asn
                20                  25                  30

Cys Asp Lys Arg Asn Leu Thr Ala Leu Pro Pro Asp Leu Pro Lys Asp
         35                  40                  45

Thr Thr Ile Leu His Leu Ser Glu Asn Leu Leu Tyr Thr Phe Ser Leu
         50                  55                  60

Ala Thr Leu Met Pro Tyr Thr Arg Leu Thr Gln Leu Asn Leu Asp Arg
 65                  70                  75                  80

Cys Glu Leu Thr Lys Leu Gln Val Asp Gly Thr Leu Pro Val Leu Gly
                 85                  90                  95

Thr Leu Asp Leu Ser His Asn Gln Leu Gln Ser Leu Pro Leu Leu Gly
                100                 105                 110

Gln Thr Leu Pro Ala Leu Thr Val Leu Asp Val Ser Phe Asn Arg Leu
            115                 120                 125
```

-continued

```
Thr Ser Leu Pro Leu Gly Ala Leu Arg Gly Leu Gly Glu Leu Gln Glu
    130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175

Thr Glu Leu Pro Ala Gly Leu Leu Asn Gly Leu Glu Asn Leu Asp Thr
                180                 185                 190

Leu Leu Leu Gln Glu Asn Ser Leu Tyr Thr Ile Pro Lys Gly Phe Phe
            195                 200                 205

Gly Ser His Leu Leu Pro Phe Ala Phe Leu His Gly Asn Pro Trp Leu
        210                 215                 220

Cys Asn Cys Glu Ile Leu Tyr Phe Arg Arg Trp Leu Gln Asp Asn Ala
225                 230                 235                 240

Glu Asn Val Tyr Val Trp Lys Gln Gly Val Asp Val Lys Ala Met Thr
                245                 250                 255

Ser Asn Val Ala Ser Val Gln Cys Asp Asn Ser Asp Lys Phe Pro Val
                260                 265                 270

Tyr Lys Tyr Pro Gly Lys Gly Cys Pro Thr Leu Gly Asp Glu Gly Asp
            275                 280                 285

Thr Asp Leu Tyr Asp Tyr Tyr Pro Glu Glu Asp Thr Glu Gly Asp Lys
        290                 295                 300

Val Ala Ala Thr Ala Thr Val Lys Phe Pro Thr Lys Ala Arg Pro
305                 310                 315                 320

His Thr Cys Pro Pro Cys Pro Ala Pro Glu Ala Leu Gly Ala Pro Ser
                325                 330                 335

Val Phe Leu Phe Pro Pro Lys Pro Lys Asp Thr Leu Met Ile Ser Arg
                340                 345                 350

Thr Pro Glu Val Thr Cys Val Val Val Asp Val Ser His Glu Asp Pro
            355                 360                 365

Glu Val Lys Phe Asn Trp Tyr Val Asp Gly Val Glu Val His Asn Ala
        370                 375                 380

Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
                405                 410                 415

Lys Cys Lys Val Ser Asn Lys Ala Leu Pro Val Pro Ile Glu Lys Thr
                420                 425                 430

Ile Ser Lys Ala Lys Gly Gln Pro Arg Glu Pro Gln Val Tyr Thr Leu
            435                 440                 445

Pro Pro Ser Arg Glu Glu Met Thr Lys Asn Gln Val Ser Leu Thr Cys
        450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
                500                 505                 510

Arg Trp Gln Gln Gly Asn Val Phe Ser Cys Ser Val Met His Glu Ala
            515                 520                 525

Leu His Asn His Tyr Thr Gln Lys Ser Leu Ser Leu Ser Pro Gly Lys
        530                 535                 540
```

-continued

```
<210> SEQ ID NO 3
<211> LENGTH: 544
<212> TYPE: PRT
<213> ORGANISM: Homo sapiens
<220> FEATURE:
<221> NAME/KEY: DOMAIN
<222> LOCATION: (1)..(544)
<223> OTHER INFORMATION: GP1b302/4X-Ig

<400> SEQUENCE: 3
```

```
Met Pro Leu Leu Leu Leu Leu Leu Leu Pro Ser Pro Leu His Pro
  1               5                  10                  15

His Pro Ile Cys Glu Val Ser Lys Val Ala Ser His Leu Glu Val Asn
                 20                  25                  30

Cys Asp Lys Arg Asn Leu Thr Ala Leu Pro Pro Asp Leu Pro Lys Asp
             35                  40                  45

Thr Thr Ile Leu His Leu Ser Glu Asn Leu Leu Tyr Thr Phe Ser Leu
         50                  55                  60

Ala Thr Leu Met Pro Tyr Thr Arg Leu Thr Gln Leu Asn Leu Asp Arg
 65                  70                  75                  80

Cys Glu Leu Thr Lys Leu Gln Val Asp Gly Thr Leu Pro Val Leu Gly
                 85                  90                  95

Thr Leu Asp Leu Ser His Asn Gln Leu Gln Ser Leu Pro Leu Leu Gly
                100                 105                 110

Gln Thr Leu Pro Ala Leu Thr Val Leu Asp Val Ser Phe Asn Arg Leu
            115                 120                 125

Thr Ser Leu Pro Leu Gly Ala Leu Arg Gly Leu Gly Glu Leu Gln Glu
        130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175

Thr Glu Leu Pro Ala Gly Leu Leu Asn Gly Leu Glu Asn Leu Asp Thr
            180                 185                 190

Leu Leu Leu Gln Glu Asn Ser Leu Tyr Thr Ile Pro Lys Gly Phe Phe
        195                 200                 205

Gly Ser His Leu Leu Pro Phe Ala Phe Leu His Gly Asn Pro Trp Leu
    210                 215                 220

Cys Asn Cys Glu Ile Leu Tyr Phe Arg Arg Trp Leu Gln Asp Asn Ala
225                 230                 235                 240

Glu Asn Val Tyr Val Trp Lys Gln Val Val Asp Val Lys Ala Val Thr
                245                 250                 255

Ser Asn Val Ala Ser Val Gln Cys Asp Asn Ser Asp Lys Phe Pro Val
            260                 265                 270

Tyr Lys Tyr Pro Gly Lys Gly Cys Pro Thr Leu Gly Asp Glu Gly Asp
        275                 280                 285

Thr Asp Leu Tyr Asp Tyr Tyr Pro Glu Glu Asp Thr Glu Gly Asp Lys
    290                 295                 300

Val Ala Ala Thr Ala Thr Val Val Lys Phe Pro Thr Lys Ala Arg Pro
305                 310                 315                 320

His Thr Cys Pro Pro Cys Pro Ala Pro Glu Ala Leu Gly Ala Pro Ser
                325                 330                 335

Val Phe Leu Phe Pro Pro Lys Pro Lys Asp Thr Leu Met Ile Ser Arg
            340                 345                 350

Thr Pro Glu Val Thr Cys Val Val Val Asp Val Ser His Glu Asp Pro
        355                 360                 365
```

-continued

```
Glu Val Lys Phe Asn Trp Tyr Val Asp Gly Val Glu Val His Asn Ala
    370                 375                 380

Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
                405                 410                 415

Lys Cys Lys Val Ser Asn Lys Ala Leu Pro Val Pro Ile Glu Lys Thr
            420                 425                 430

Ile Ser Lys Ala Lys Gly Gln Pro Arg Glu Pro Gln Val Tyr Thr Leu
        435                 440                 445

Pro Pro Ser Arg Glu Glu Met Thr Lys Asn Gln Val Ser Leu Thr Cys
    450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
        515                 520                 525

Leu His Asn His Tyr Thr Gln Lys Ser Leu Ser Leu Ser Pro Gly Lys
    530                 535                 540

<210> SEQ ID NO 4
<211> LENGTH: 531
<212> TYPE: PRT
<213> ORGANISM: Homo sapiens
<220> FEATURE:
<221> NAME/KEY: DOMAIN
<222> LOCATION: (1)..(531)
<223> OTHER INFORMATION: GP1b290-Ig

<400> SEQUENCE: 4

Met Pro Leu Leu Leu Leu Leu Leu Leu Pro Ser Pro Leu His Pro
  1               5                  10                  15

His Pro Ile Cys Glu Val Ser Lys Val Ala Ser His Leu Glu Val Asn
                20                  25                  30

Cys Asp Lys Arg Asn Leu Thr Ala Leu Pro Pro Asp Leu Pro Lys Asp
            35                  40                  45

Thr Thr Ile Leu His Leu Ser Glu Asn Leu Leu Tyr Thr Phe Ser Leu
        50                  55                  60

Ala Thr Leu Met Pro Tyr Thr Arg Leu Thr Gln Leu Asn Leu Asp Arg
65                  70                  75                  80

Cys Glu Leu Thr Lys Leu Gln Val Asp Gly Thr Leu Pro Val Leu Gly
                85                  90                  95

Thr Leu Asp Leu Ser His Asn Gln Leu Gln Ser Leu Pro Leu Leu Gly
            100                 105                 110

Gln Thr Leu Pro Ala Leu Thr Val Leu Asp Val Ser Phe Asn Arg Leu
        115                 120                 125

Thr Ser Leu Pro Leu Gly Ala Leu Arg Gly Leu Gly Glu Leu Gln Glu
    130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175
```

```
Thr Glu Leu Pro Ala Gly Leu Leu Asn Gly Leu Glu Asn Leu Asp Thr
            180                 185                 190
Leu Leu Leu Gln Glu Asn Ser Leu Tyr Thr Ile Pro Lys Gly Phe Phe
        195                 200                 205
Gly Ser His Leu Leu Pro Phe Ala Phe Leu His Gly Asn Pro Trp Leu
    210                 215                 220
Cys Asn Cys Glu Ile Leu Tyr Phe Arg Arg Trp Leu Gln Asp Asn Ala
225                 230                 235                 240
Glu Asn Val Tyr Val Trp Lys Gln Gly Val Asp Val Lys Ala Met Thr
                245                 250                 255
Ser Asn Val Ala Ser Val Gln Cys Asp Asn Ser Asp Lys Phe Pro Val
            260                 265                 270
Tyr Lys Tyr Pro Gly Lys Gly Cys Pro Thr Leu Gly Asp Glu Gly Asp
        275                 280                 285
Thr Asp Leu Tyr Asp Tyr Tyr Pro Glu Glu Asp Thr Glu Gly Asp Lys
    290                 295                 300
Val Arg Pro His Thr Cys Pro Pro Cys Pro Ala Pro Glu Ala Leu Gly
305                 310                 315                 320
Ala Pro Ser Val Phe Leu Phe Pro Pro Lys Pro Lys Asp Thr Leu Met
                325                 330                 335
Ile Ser Arg Thr Pro Glu Val Thr Cys Val Val Val Asp Val Ser His
            340                 345                 350
Glu Asp Pro Glu Val Lys Phe Asn Trp Tyr Val Asp Gly Val Glu Val
        355                 360                 365
His Asn Ala Lys Thr Lys Pro Arg Glu Glu Gln Tyr Asn Ser Thr Tyr
    370                 375                 380
Arg Val Val Ser Val Leu Thr Val Leu His Gln Asp Trp Leu Asn Gly
385                 390                 395                 400
Lys Glu Tyr Lys Cys Lys Val Ser Asn Lys Ala Leu Pro Val Pro Ile
                405                 410                 415
Glu Lys Thr Ile Ser Lys Ala Lys Gly Gln Pro Arg Glu Pro Gln Val
            420                 425                 430
Tyr Thr Leu Pro Pro Ser Arg Glu Glu Met Thr Lys Asn Gln Val Ser
        435                 440                 445
Leu Thr Cys Leu Val Lys Gly Phe Tyr Pro Ser Asp Ile Ala Val Glu
    450                 455                 460
Trp Glu Ser Asn Gly Gln Pro Glu Asn Asn Tyr Lys Thr Thr Pro Pro
465                 470                 475                 480
Val Leu Asp Ser Asp Gly Ser Phe Phe Leu Tyr Ser Lys Leu Thr Val
                485                 490                 495
Asp Lys Ser Arg Trp Gln Gln Gly Asn Val Phe Ser Cys Ser Val Met
            500                 505                 510
His Glu Ala Leu His Asn His Tyr Thr Gln Lys Ser Leu Ser Leu Ser
        515                 520                 525
Pro Gly Lys
    530

<210> SEQ ID NO 5
<211> LENGTH: 531
<212> TYPE: PRT
<213> ORGANISM: Homo sapiens
<220> FEATURE:
<221> NAME/KEY: DOMAIN
<222> LOCATION: (1)..(531)
<223> OTHER INFORMATION: GP1b290/2V-Ig
```

```
<400> SEQUENCE: 5

Met Pro Leu Leu Leu Leu Leu Leu Leu Pro Ser Pro Leu His Pro
 1               5                  10                  15

His Pro Ile Cys Glu Val Ser Lys Val Ala Ser His Leu Glu Val Asn
             20                  25                  30

Cys Asp Lys Arg Asn Leu Thr Ala Leu Pro Pro Asp Leu Pro Lys Asp
             35                  40                  45

Thr Thr Ile Leu His Leu Ser Glu Asn Leu Leu Tyr Thr Phe Ser Leu
         50                  55                  60

Ala Thr Leu Met Pro Tyr Thr Arg Leu Thr Gln Leu Asn Leu Asp Arg
 65                  70                  75                  80

Cys Glu Leu Thr Lys Leu Gln Val Asp Gly Thr Leu Pro Val Leu Gly
                 85                  90                  95

Thr Leu Asp Leu Ser His Asn Gln Leu Gln Ser Leu Pro Leu Leu Gly
                100                 105                 110

Gln Thr Leu Pro Ala Leu Thr Val Leu Asp Val Ser Phe Asn Arg Leu
                115                 120                 125

Thr Ser Leu Pro Leu Gly Ala Leu Arg Gly Leu Gly Glu Leu Gln Glu
        130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175

Thr Glu Leu Pro Ala Gly Leu Leu Asn Gly Leu Glu Asn Leu Asp Thr
                180                 185                 190

Leu Leu Leu Gln Glu Asn Ser Leu Tyr Thr Ile Pro Lys Gly Phe Phe
            195                 200                 205

Gly Ser His Leu Leu Pro Phe Ala Phe Leu His Gly Asn Pro Trp Leu
        210                 215                 220

Cys Asn Cys Glu Ile Leu Tyr Phe Arg Arg Trp Leu Gln Asp Asn Ala
225                 230                 235                 240

Glu Asn Val Tyr Val Trp Lys Gln Val Val Asp Val Lys Ala Val Thr
                245                 250                 255

Ser Asn Val Ala Ser Val Gln Cys Asp Asn Ser Asp Lys Phe Pro Val
                260                 265                 270

Tyr Lys Tyr Pro Gly Lys Gly Cys Pro Thr Leu Gly Asp Glu Gly Asp
            275                 280                 285

Thr Asp Leu Tyr Asp Tyr Pro Glu Glu Asp Thr Glu Gly Asp Lys
            290                 295                 300

Val Arg Pro His Thr Cys Pro Pro Cys Pro Ala Pro Glu Ala Leu Gly
305                 310                 315                 320

Ala Pro Ser Val Phe Leu Phe Pro Pro Lys Pro Lys Asp Thr Leu Met
                325                 330                 335

Ile Ser Arg Thr Pro Glu Val Thr Cys Val Val Val Asp Val Ser His
            340                 345                 350

Glu Asp Pro Glu Val Lys Phe Asn Trp Tyr Val Asp Gly Val Glu Val
            355                 360                 365

His Asn Ala Lys Thr Lys Pro Arg Glu Glu Gln Tyr Asn Ser Thr Tyr
        370                 375                 380

Arg Val Val Ser Val Leu Thr Val Leu His Gln Asp Trp Leu Asn Gly
385                 390                 395                 400

Lys Glu Tyr Lys Cys Lys Val Ser Asn Lys Ala Leu Pro Val Pro Ile
                405                 410                 415
```

-continued

```
Glu Lys Thr Ile Ser Lys Ala Lys Gly Gln Pro Arg Glu Pro Gln Val
            420                 425                 430

Tyr Thr Leu Pro Pro Ser Arg Glu Glu Met Thr Lys Asn Gln Val Ser
        435                 440                 445

Leu Thr Cys Leu Val Lys Gly Phe Tyr Pro Ser Asp Ile Ala Val Glu
    450                 455                 460

Trp Glu Ser Asn Gly Gln Pro Glu Asn Asn Tyr Lys Thr Thr Pro Pro
465                 470                 475                 480

Val Leu Asp Ser Asp Gly Ser Phe Phe Leu Tyr Ser Lys Leu Thr Val
                485                 490                 495

Asp Lys Ser Arg Trp Gln Gln Gly Asn Val Phe Ser Cys Ser Val Met
            500                 505                 510

His Glu Ala Leu His Asn His Tyr Thr Gln Lys Ser Leu Ser Leu Ser
        515                 520                 525

Pro Gly Lys
    530

<210> SEQ ID NO 6
<211> LENGTH: 531
<212> TYPE: PRT
<213> ORGANISM: Homo sapiens
<220> FEATURE:
<221> NAME/KEY: DOMAIN
<222> LOCATION: (1)..(531)
<223> OTHER INFORMATION: GP1b290/1A-Ig

<400> SEQUENCE: 6

Met Pro Leu Leu Leu Leu Leu Leu Leu Pro Ser Pro Leu His Pro
 1               5                  10                  15

His Pro Ile Cys Glu Val Ser Lys Val Ala Ser His Leu Glu Val Asn
                20                  25                  30

Cys Asp Lys Arg Asn Leu Thr Ala Leu Pro Pro Asp Leu Pro Lys Asp
            35                  40                  45

Thr Thr Ile Leu His Leu Ser Glu Asn Leu Leu Tyr Thr Phe Ser Leu
    50                  55                  60

Ala Thr Leu Met Pro Tyr Thr Arg Leu Thr Gln Leu Asn Leu Asp Arg
65                  70                  75                  80

Cys Glu Leu Thr Lys Leu Gln Val Asp Gly Thr Leu Pro Val Leu Gly
                85                  90                  95

Thr Leu Asp Leu Ser His Asn Gln Leu Gln Ser Leu Pro Leu Leu Gly
            100                 105                 110

Gln Thr Leu Pro Ala Leu Thr Val Leu Asp Val Ser Phe Asn Arg Leu
    115                 120                 125

Thr Ser Leu Pro Leu Gly Ala Leu Arg Gly Leu Gly Glu Leu Gln Glu
130                 135                 140

Leu Tyr Leu Lys Gly Asn Glu Leu Lys Thr Leu Pro Pro Gly Leu Leu
                145                 150                 155                 160

Thr Pro Thr Pro Lys Leu Glu Lys Leu Ser Leu Ala Asn Asn Asn Leu
            165                 170                 175

Thr Glu Leu Pro Ala Gly Leu Leu Asn Gly Leu Glu Asn Leu Asp Thr
    180                 185                 190

Leu Leu Leu Gln Glu Asn Ser Leu Tyr Thr Ile Pro Lys Gly Phe Phe
195                 200                 205

Gly Ser His Leu Leu Pro Phe Ala Phe Leu His Gly Asn Pro Trp Leu
    210                 215                 220
```

-continued

```
Cys Asn Cys Glu Ile Leu Tyr Phe Arg Arg Trp Leu Gln Asp Asn Ala
225                 230                 235                 240

Glu Asn Val Tyr Val Trp Lys Gln Gly Val Asp Val Ala Ala Met Thr
            245                 250                 255

Ser Asn Val Ala Ser Val Gln Cys Asp Asn Ser Asp Lys Phe Pro Val
        260                 265                 270

Tyr Lys Tyr Pro Gly Lys Gly Cys Pro Thr Leu Gly Asp Glu Gly Asp
    275                 280                 285

Thr Asp Leu Tyr Asp Tyr Tyr Pro Glu Glu Asp Thr Glu Gly Asp Lys
290                 295                 300

Val Arg Pro His Thr Cys Pro Pro Cys Pro Ala Pro Glu Ala Leu Gly
305                 310                 315                 320

Ala Pro Ser Val Phe Leu Phe Pro Pro Lys Pro Lys Asp Thr Leu Met
            325                 330                 335

Ile Ser Arg Thr Pro Glu Val Thr Cys Val Val Val Asp Val Ser His
        340                 345                 350

Glu Asp Pro Glu Val Lys Phe Asn Trp Tyr Val Asp Gly Val Glu Val
    355                 360                 365

His Asn Ala Lys Thr Lys Pro Arg Glu Glu Gln Tyr Asn Ser Thr Tyr
370                 375                 380

Arg Val Val Ser Val Leu Thr Val Leu His Gln Asp Trp Leu Asn Gly
385                 390                 395                 400

Lys Glu Tyr Lys Cys Lys Val Ser Asn Lys Ala Leu Pro Val Pro Ile
            405                 410                 415

Glu Lys Thr Ile Ser Lys Ala Lys Gly Gln Pro Arg Glu Pro Gln Val
        420                 425                 430

Tyr Thr Leu Pro Pro Ser Arg Glu Glu Met Thr Lys Asn Gln Val Ser
    435                 440                 445

Leu Thr Cys Leu Val Lys Gly Phe Tyr Pro Ser Asp Ile Ala Val Glu
450                 455                 460

Trp Glu Ser Asn Gly Gln Pro Glu Asn Asn Tyr Lys Thr Thr Pro Pro
465                 470                 475                 480

Val Leu Asp Ser Asp Gly Ser Phe Phe Leu Tyr Ser Lys Leu Thr Val
            485                 490                 495

Asp Lys Ser Arg Trp Gln Gln Gly Asn Val Phe Ser Cys Ser Val Met
        500                 505                 510

His Glu Ala Leu His Asn His Tyr Thr Gln Lys Ser Leu Ser Leu Ser
    515                 520                 525

Pro Gly Lys
    530
```

<210> SEQ ID NO 7
<211> LENGTH: 302
<212> TYPE: PRT
<213> ORGANISM: Homo sapiens
<220> FEATURE:
<221> NAME/KEY: DOMAIN
<222> LOCATION: (1)..(302)
<223> OTHER INFORMATION: GP1b302

<400> SEQUENCE: 7

```
His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
```

-continued

```
                35                  40                  45
Ala Thr Leu Met Pro Tyr Thr Arg Leu Thr Gln Leu Asn Leu Asp Arg
 50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Ala Thr Arg Thr Val Val Lys Phe Pro Thr Lys Ala
290                 295                 300
```

<210> SEQ ID NO 8
<211> LENGTH: 302
<212> TYPE: PRT
<213> ORGANISM: Homo sapiens
<220> FEATURE:
<221> NAME/KEY: DOMAIN
<222> LOCATION: (1)..(302)
<223> OTHER INFORMATION: GP1b302/2A

<400> SEQUENCE: 8

```
His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
 50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95
```

-continued

```
Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Ala Ala Thr Ala Thr Val Val Lys Phe Pro Thr Lys Ala
    290                 295                 300

<210> SEQ ID NO 9
<211> LENGTH: 301
<212> TYPE: PRT
<213> ORGANISM: Homo sapiens
<220> FEATURE:
<221> NAME/KEY: DOMAIN
<222> LOCATION: (1)..(301)
<223> OTHER INFORMATION: GP1b/4X

<400> SEQUENCE: 9

His Pro Ile Cys Glu Val Ser Lys Val Ala Ser His Leu Glu Val Asn
 1               5                  10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140
```

-continued

```
Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
            165                 170                 175

Leu Leu Leu Gln Glu Asn Ser Leu Tyr Thr Ile Pro Lys Gly Phe Phe
        180                 185                 190

Gly Ser His Leu Leu Pro Phe Ala Phe Leu His Gly Asn Pro Trp Leu
    195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Val Val Asp Val Lys Ala Val Thr
225                 230                 235                 240

Ser Asn Val Ala Ser Val Gln Cys Asp Asn Ser Asp Lys Phe Pro Val
                245                 250                 255

Lys Tyr Pro Gly Lys Gly Cys Pro Thr Leu Gly Asp Glu Gly Asp Thr
            260                 265                 270

Asp Leu Tyr Asp Tyr Tyr Pro Glu Glu Asp Thr Glu Gly Asp Lys Val
        275                 280                 285

Ala Ala Thr Ala Thr Val Val Lys Phe Pro Thr Lys Ala
    290                 295                 300

<210> SEQ ID NO 10
<211> LENGTH: 290
<212> TYPE: PRT
<213> ORGANISM: Homo sapiens
<220> FEATURE:
<221> NAME/KEY: DOMAIN
<222> LOCATION: (1)..(290)
<223> OTHER INFORMATION: GP1b290

<400> SEQUENCE: 10

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
            165                 170                 175

Leu Leu Leu Gln Glu Asn Ser Leu Tyr Thr Ile Pro Lys Gly Phe Phe
        180                 185                 190

Gly Ser His Leu Leu Pro Phe Ala Phe Leu His Gly Asn Pro Trp Leu
```

```
                  195                 200                 205
Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Pro Glu Glu Asp Thr Glu Gly Asp Lys
        275                 280                 285

Val Arg
    290

<210> SEQ ID NO 11
<211> LENGTH: 290
<212> TYPE: PRT
<213> ORGANISM: Homo sapiens
<220> FEATURE:
<221> NAME/KEY: DOMAIN
<222> LOCATION: (1)..(290)
<223> OTHER INFORMATION: GB1b290/2V

<400> SEQUENCE: 11

His Pro Ile Cys Glu Val Ser Lys Val Ala Ser His Leu Glu Val Asn
  1               5                  10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
    50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Val Thr
225                 230                 235                 240

Ser Asn Val Ala Ser Val Gln Cys Asp Asn Ser Asp Lys Phe Pro Val
                245                 250                 255
```

```
Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg
    290

<210> SEQ ID NO 12
<211> LENGTH: 290
<212> TYPE: PRT
<213> ORGANISM: Homo sapiens
<220> FEATURE:
<221> NAME/KEY: DOMAIN
<222> LOCATION: (1)..(290)
<223> OTHER INFORMATION: GB1b290/1A

<400> SEQUENCE: 12

His Pro Ile Cys Glu Val Ser Lys Val Ala Ser His Leu Glu Val Asn
  1               5                  10                  15

Cys Asp Lys Arg Asn Leu Thr Ala Leu Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
     50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Ala Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg
    290
```

-continued

```
<210> SEQ ID NO 13
<211> LENGTH: 16
<212> TYPE: PRT
<213> ORGANISM: Homo sapiens
<220> FEATURE:
<221> NAME/KEY: DOMAIN
<222> LOCATION: (1)..(16)
<223> OTHER INFORMATION: Signal Peptide

<400> SEQUENCE: 13

Met Pro Leu Leu Leu Leu Leu Leu Leu Pro Ser Pro Leu His Pro
 1               5                  10                  15

<210> SEQ ID NO 14
<211> LENGTH: 224
<212> TYPE: PRT
<213> ORGANISM: Homo sapiens
<220> FEATURE:
<221> NAME/KEY: DOMAIN
<222> LOCATION: (1)..(224)

<400> SEQUENCE: 14

His Thr Cys Pro Pro Cys Pro Ala Pro Glu Ala Leu Gly Ala Pro Ser
 1               5                  10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Val Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 15
<211> LENGTH: 1632
<212> TYPE: DNA
<213> ORGANISM: Homo sapiens

<400> SEQUENCE: 15
atgcctctcc tcctcttgct gctcctgctg ccaagcccct tacaccccca ccccatctgt      60
gaggtctcca aagtggccag ccacctagaa gtgaactgtg acaagaggaa tctgacagcg     120
```

```
ctgcctccag acctgccgaa agacacaacc atcctccacc tgagtgagaa cctcctgtac    180
accttctccc tggcaaccct gatgccttac actcgcctca ctcagctgaa cctagatagg    240
tgcgagctca ccaagctcca ggtcgatggg acgctgccag tgctggggac cctggatcta    300
tcccacaatc agctgcaaag cctgcccttg ctagggcaga cactgcctgc tctcaccgtc    360
ctggacgtct ccttcaaccg gctgacctcg ctgcctcttg gtgccctgcg tggtcttggc    420
gaactccaag agctctacct gaaaggcaat gagctgaaga ccctgccccc agggctcctg    480
acgcccacac ccaagctgga gaagctcagt ctggctaaca caacttgac tgagctcccc     540
gctgggctcc tgaatgggct ggagaatctc gacacccttc tcctccaaga gaactcgctg    600
tatacaatac caaagggctt ttttgggtcc cacctcctgc cttttgcttt tctccacggg    660
aaccccctggt tatgcaactg tgagatcctc tatttttcgtc gctggctgca ggacaatgct  720
gaaaatgtct acgtatggaa gcaaggtgtg acgtcaagg ccatgacctc taacgtggcc     780
agtgtgcagt gtgacaattc agacaagttt cccgtctaca atacccagg aaagggtgc     840
cccacccttg gtgatgaagg tgacacagac ctatatgatt actacccaga gaggacact    900
gagggcgata aggtgcgtgc cacaaggact gtggtcaagt tccccaccaa agcgcggccg    960
cacacatgcc caccgtgccc agcacctgaa gccctggggg gaccgtcagt cttcctcttc   1020
ccccccaaaac ccaaggacac cctcatgatc tcccggaccc ctgaggtcac atgcgtggtg   1080
gtggacgtga gccacgaaga ccctgaggtc aagttcaact ggtacgtgga cggcgtggag   1140
gtgcataatg ccaagacaaa gccgcgggag gagcagtaca acagcacgta ccgtgtggtc   1200
agcgtcctca ccgtcctgca ccaggactgg ctgaatggca aggagtacaa gtgcaaggtc   1260
tccaacaaag ccctcccagt ccccatcgag aaaaccatct ccaaagccaa agggcagccc   1320
cgagaaccac aggtgtacac cctgccccca tcccgggagg agatgaccaa gaaccaggtc   1380
agcctgacct gcctggtcaa aggcttctat cccagcgaca tcgccgtgga gtgggagagc   1440
aatgggcagc cggagaacaa ctacaagacc acgcctcccg tgctggactc cgacggcccc   1500
ttcttcctct acagcaagct caccgtggac aagagcaggt ggcagcaggg gaacgtcttc   1560
tcatgctccg tgatgcatga ggctctgcac aaccactaca cgcagaagag cctctccctg   1620
tctccgggta aa                                                       1632

<210> SEQ ID NO 16
<211> LENGTH: 1632
<212> TYPE: DNA
<213> ORGANISM: Homo sapiens

<400> SEQUENCE: 16
atgcctctcc tcctcttgct gctcctgctg ccaagcccct acacccccca ccccatctgt     60
gaggtctcca aagtggccag ccacctagaa gtgaactgtg acaagaggaa tctgacagcg    120
ctgcctccag acctgccgaa agacacaacc atcctccacc tgagtgagaa cctcctgtac    180
accttctccc tggcaaccct gatgccttac actcgcctca ctcagctgaa cctagatagg    240
tgcgagctca ccaagctcca ggtcgatggg acgctgccag tgctggggac cctggatcta    300
tcccacaatc agctgcaaag cctgcccttg ctagggcaga cactgcctgc tctcaccgtc    360
ctggacgtct ccttcaaccg gctgacctcg ctgcctcttg gtgccctgcg tggtcttggc    420
gaactccaag agctctacct gaaaggcaat gagctgaaga ccctgccccc agggctcctg    480
acgcccacac ccaagctgga gaagctcagt ctggctaaca caacttgac tgagctcccc     540
```

| | |
|---|---|
| gctgggctcc tgaatgggct ggagaatctc gacacccttc tcctccaaga gaactcgctg | 600 |
| tatacaatac caaagggctt ttttgggtcc cacctcctgc cttttgcttt tctccacggg | 660 |
| aacccctggt tatgcaactg tgagatcctc tattttcgtc gctggctgca ggacaatgct | 720 |
| gaaaatgtct acgtatggaa gcaaggtgtg gacgtcaagg ccatgacctc taacgtggcc | 780 |
| agtgtgcagt gtgacaattc agacaagttt cccgtctaca aatacccagg aaagggtgc | 840 |
| cccacccttg gtgatgaagg tgacacagac ctatatgatt actacccaga agaggacact | 900 |
| gagggcgata agtggctgc cacagcgact gtggtcaagt tccccaccaa agcgcggccg | 960 |
| cacacatgcc caccgtgccc agcacctgaa gccctggggg caccgtcagt cttcctcttc | 1020 |
| cccccaaaac ccaaggacac cctcatgatc tcccggaccc ctgaggtcac atgcgtggtg | 1080 |
| gtggacgtga gccacgaaga ccctgaggtc aagttcaact ggtacgtgga cggcgtggag | 1140 |
| gtgcataatg ccaagacaaa gccgcgggag gagcagtaca acagcacgta ccgtgtggtc | 1200 |
| agcgtcctca ccgtcctgca ccaggactgg ctgaatggca aggagtacaa gtgcaaggtc | 1260 |
| tccaacaaag ccctcccagt ccccatcgag aaaaccatct ccaaagccaa agggcagccc | 1320 |
| cgagaaccac aggtgtacac cctgccccca tcccgggagg agatgaccaa gaaccaggtc | 1380 |
| agcctgacct gcctggtcaa aggcttctat cccagcgaca tcgccgtgga gtgggagagc | 1440 |
| aatgggcagc cggagaacaa ctacaagacc acgcctcccg tgctggactc cgacggcccc | 1500 |
| ttcttcctct acagcaagct caccgtggac aagagcaggt ggcagcaggg gaacgtcttc | 1560 |
| tcatgctccg tgatgcatga ggctctgcac aaccactaca cgcagaagag cctctccctg | 1620 |
| tctccgggta aa | 1632 |

<210> SEQ ID NO 17
<211> LENGTH: 1632
<212> TYPE: DNA
<213> ORGANISM: Homo sapiens

<400> SEQUENCE: 17

| | |
|---|---|
| atgcctctcc tcctcttgct gctcctgctg ccaagcccct acacccccca ccccatctgt | 60 |
| gaggtctcca aagtggccag ccacctagaa gtgaactgtg acaagaggaa tctgacagcg | 120 |
| ctgcctccag acctgccgaa agacacaacc atcctccacc tgagtgagaa cctcctgtac | 180 |
| accttctccc tggcaaccct gatgccttac actcgcctca ctcagctgaa cctagatagg | 240 |
| tgcgagctca ccaagctcca ggtcgatggg acgctgccag tgctggggac cctggatcta | 300 |
| tcccacaatc agctgcaaag cctgcccttg ctagggcaga cactgcctgc tctcaccgtc | 360 |
| ctggacgtct ccttcaaccg gctgacctcg ctgcctcttg gtgccctgcg tggtcttggc | 420 |
| gaactccaag agctctacct gaaaggcaat gagctgaaga ccctgccccc agggctcctg | 480 |
| acgcccacac ccaagctgga gaagctcagt ctggctaaca caacttgac tgagctcccc | 540 |
| gctgggctcc tgaatgggct ggagaatctc gacacccttc tcctccaaga gaactcgctg | 600 |
| tatacaatac caaagggctt ttttgggtcc cacctcctgc cttttgcttt tctccacggg | 660 |
| aacccctggt tatgcaactg tgagatcctc tattttcgtc gctggctgca ggacaatgct | 720 |
| gaaaatgtct acgtatggaa gcaagtggtg gacgtcaagg ccgtgacctc taacgtggcc | 780 |
| agtgtgcagt gtgacaattc agacaagttt cccgtctaca aatacccagg aaagggtgc | 840 |
| cccacccttg gtgatgaagg tgacacagac ctatatgatt actacccaga agaggacact | 900 |
| gagggcgata agtggctgc cacagcgact gtggtcaagt tccccaccaa agcgcggccg | 960 |
| cacacatgcc caccgtgccc agcacctgaa gccctggggg caccgtcagt cttcctcttc | 1020 |

-continued

```
cccccaaaac ccaaggacac cctcatgatc tcccggaccc ctgaggtcac atgcgtggtg      1080
gtggacgtga gccacgaaga ccctgaggtc aagttcaact ggtacgtgga cggcgtggag      1140
gtgcataatg ccaagacaaa gccgcgggag gagcagtaca acagcacgta ccgtgtggtc      1200
agcgtcctca ccgtcctgca ccaggactgg ctgaatggca aggagtacaa gtgcaaggtc      1260
tccaacaaag ccctcccagt ccccatcgag aaaaccatct ccaaagccaa agggcagccc      1320
cgagaaccac aggtgtacac cctgccccca tcccgggagg agatgaccaa gaaccaggtc      1380
agcctgacct gcctggtcaa aggcttctat cccagcgaca tcgccgtgga gtgggagagc      1440
aatgggcagc cggagaacaa ctacaagacc acgcctcccg tgctggactc cgacggcccc      1500
ttcttcctct acagcaagct caccgtggac aagagcaggt ggcagcaggg gaacgtcttc      1560
tcatgctccg tgatgcatga ggctctgcac aaccactaca cgcagaagag cctctccctg      1620
tctccgggta aa                                                          1632

<210> SEQ ID NO 18
<211> LENGTH: 1593
<212> TYPE: DNA
<213> ORGANISM: Homo sapiens

<400> SEQUENCE: 18
atgcctctcc tcctcttgct gctcctgctg ccaagcccct acaccccca ccccatctgt        60 gaggtctcca aagtggccag ccacctagaa gtgaactgtg acaagaggaa tctgacagcg       120
ctgcctccag acctgcgaa agacacaacc atcctccacc tgagtgagaa cctcctgtac        180
accttctccc tggcaaccct gatgcctac actcgcctca ctcagctgaa cctagatagg        240
tgcgagctca ccaagctcca ggtcgatggg acgctgccag tgctggggac cctggatcta       300
tcccacaatc agctgcaaag cctgcccttg ctagggcaga cactgcctgc tctcaccgtc       360
ctggacgtct ccttcaaccg gctgacctcg ctgcctcttg gtgccctgcg tggtcttggc       420
gaactccaag agctctacct gaaaggcaat gagctgaaga ccctgccccc agggctcctg       480
acgcccacac ccaagctgga gaagctcagt ctggctaaca caacttgac tgagctcccc       540 gctgggctcc tgaatgggct ggagaatctc gacacccttc tcctccaaga gaactcgctg       600
tatacaatac aaagggcttt ttggggtcc cacctcctgc cttttgcttt tctccacggg       660 aaccccctggt tatgcaactg tgagatcctc tattttcgtc gctggctgca ggacaatgct       720
gaaaatgtct acgtatggaa gcaaggtgtg acgtcaagg ccatgacctc taacgtggcc        780
agtgtgcagt gtgacaattc agacaagttt cccgtctaca atacccagg aaagggggtgc      840 cccacccttg tgatgaaggt gacacagac ctatatgatt actacccaga gaggacact         900 gagggcgata aggtgcggcc gcacacatgc ccaccgtgcc cagcacctga gccctgggg       960 gcaccgtcag tcttcctctt ccccccaaaa cccaaggaca ccctcatgat ctcccggacc      1020
cctgaggtca catgcgtggt ggtggacgtg agccacgaag accctgaggt caagttcaac      1080
tggtacgtgg acggcgtgga ggtgcataat gccaagacaa agccgcggga ggagcagtac      1140
aacagcacgt accgtgtggt cagcgtcctc accgtcctgc accaggactg gctgaatggc      1200
aaggagtaca agtgcaaggt ctccaacaaa gccctcccag tccccatcga gaaaaccatc      1260
tccaaagcca aagggcagcc ccgagaacca caggtgtaca ccctgccccc atcccgggag      1320
gagatgacca agaaccaggt cagcctgacc tgcctggtca aaggcttcta tcccagcgac      1380
atcgccgtgg agtgggagag caatgggcag ccggagaaca actacaagac cacgcctccc      1440
```

| | |
|---|---:|
| gtgctggact ccgacggccc cttcttcctc tacagcaagc tcaccgtgga caagagcagg | 1500 |
| tggcagcagg ggaacgtctt ctcatgctcc gtgatgcatg aggctctgca caaccactac | 1560 |
| acgcagaaga gcctctccct gtctccgggt aaa | 1593 |

<210> SEQ ID NO 19
<211> LENGTH: 1593
<212> TYPE: DNA
<213> ORGANISM: Homo sapiens

<400> SEQUENCE: 19

| | |
|---|---:|
| atgcctctcc tcctcttgct gctcctgctg ccaagcccct acaccccca ccccatctgt | 60 |
| gaggtctcca aagtggccag ccacctagaa gtgaactgtg acaagaggaa tctgacagcg | 120 |
| ctgcctccag acctgccgaa agacacaacc atcctccacc tgagtgagaa cctcctgtac | 180 |
| accttctccc tggcaaccct gatgccttac actcgcctca ctcagctgaa cctagatagg | 240 |
| tgcgagctca ccaagctcca ggtcgatggg acgctgccag tgctggggac cctggatcta | 300 |
| tcccacaatc agctgcaaag cctgccttg ctagggcaga cactgcctgc tctcaccgtc | 360 |
| ctggacgtct ccttcaaccg gctgacctcg ctgcctcttg gtgccctgcg tggtcttggc | 420 |
| gaactccaag agctctacct gaaaggcaat gagctgaaga ccctgccccc agggctcctg | 480 |
| acgcccacac ccaagctgga gagctcagt ctggctaaca caacttgac tgagctcccc | 540 |
| gctgggctcc tgaatgggct ggagaatctc gacacccttc cctccaaga gaactcgctg | 600 |
| tatacaatac caaagggctt ttttgggtcc cacctcctgc cttttgcttt tctccacggg | 660 |
| aaccctggt tatgcaactg tgagatcctc tattttcgtc gctggctgca ggacaatgct | 720 |
| gaaaatgtct acgtatggaa gcaagtggtg gacgtcaagg ccgtgacctc taacgtggcc | 780 |
| agtgtgcagt gtgacaattc agacaagttt cccgtctaca ataccagg aaagggtgc | 840 |
| cccacccttg gtgatgaagg tgacacagac ctatatgatt actacccaga gaggacact | 900 |
| gagggcgata aggtgcggcc gcacacatgc ccaccgtgcc cagcacctga gccctgggg | 960 |
| gcaccgtcag tcttcctctt ccccccaaaa cccaaggaca cccctcatgat ctcccggacc | 1020 |
| cctgaggtca catgcgtggt ggtggacgtg agccacgaag accctgaggt caagttcaac | 1080 |
| tggtacgtgg acggcgtgga ggtgcataat gccaagacaa agccgcggga ggagcagtac | 1140 |
| aacagcacgt accgtgtggt cagcgtcctc accgtcctgc accaggactg gctgaatggc | 1200 |
| aaggagtaca agtgcaaggt ctccaacaaa gccctcccag tccccatcga gaaaaccatc | 1260 |
| tccaaagcca aagggcagcc ccgagaacca caggtgtaca ccctgccccc atcccgggag | 1320 |
| gagatgacca agaaccaggt cagcctgacc tgcctggtca aaggcttcta tcccagcgac | 1380 |
| atcgccgtgg agtgggagag caatgggcag ccggagaaca actacaagac cacgcctccc | 1440 |
| gtgctggact ccgacggccc cttcttcctc tacagcaagc tcaccgtgga caagagcagg | 1500 |
| tggcagcagg ggaacgtctt ctcatgctcc gtgatgcatg aggctctgca caaccactac | 1560 |
| acgcagaaga gcctctccct gtctccgggt aaa | 1593 |

<210> SEQ ID NO 20
<211> LENGTH: 1593
<212> TYPE: DNA
<213> ORGANISM: Homo sapiens

<400> SEQUENCE: 20

| | |
|---|---:|
| atgcctctcc tcctcttgct gctcctgctg ccaagcccct acaccccca ccccatctgt | 60 |
| gaggtctcca aagtggccag ccacctagaa gtgaactgtg acaagaggaa tctgacagcg | 120 |

-continued

```
ctgcctccag acctgccgaa agacacaacc atcctccacc tgagtgagaa cctcctgtac    180
accttctccc tggcaaccct gatgccttac actcgcctca ctcagctgaa cctagatagg    240
tgcgagctca ccaagctcca ggtcgatggg acgctgccag tgctggggac cctggatcta    300
tcccacaatc agctgcaaag cctgcccttg ctagggcaga cactgcctgc tctcaccgtc    360
ctggacgtct ccttcaaccg gctgacctcg ctgcctcttg gtgccctgcg tggtcttggc    420
gaactccaag agctctacct gaaaggcaat gagctgaaga ccctgccccc agggctcctg    480
acgcccacac ccaagctgga gaagctcagt ctggctaaca acaacttgac tgagctcccc    540
gctgggctcc tgaatgggct ggagaatctc gacacccttc tcctccaaga gaactcgctg    600
tatacaatac caaagggctt ttttgggtcc cacctcctgc cttttgcttt tctccacggg    660 aaccctggt tatgcaactg tgagatcctc tattttcgtc gctggctgca ggacaatgct    720
gaaaatgtct acgtatggaa gcaaggtgtg gacgtcgcgg ccatgacctc taacgtggcc    780
agtgtgcagt gtgacaattc agacaagttt cccgtctaca aatacccagg aaaggggtgc    840 cccaccctg gtgatgaagg tgacacagac ctatatgatt actacccaga agaggacact    900
gagggcgata aggtgcggcc gcacacatgc ccaccgtgcc cagcacctga gccctgggg    960 gcaccgtcag tcttcctctt ccccccaaaa cccaaggaca ccctcatgat ctcccggacc   1020
cctgaggtca catgcgtggt ggtggacgtg agccacgaag accctgaggt caagttcaac   1080
tggtacgtgg acggcgtgga ggtgcataat gccaagacaa agccgcggga ggagcagtac   1140
aacagcacgt accgtgtggt cagcgtcctc accgtcctgc accaggactg gctgaatggc   1200
aaggagtaca agtgcaaggt ctccaacaaa gccctcccag tccccatcga gaaaaccatc   1260
tccaaagcca aagggcagcc ccgagaacca caggtgtaca ccctgccccc atcccgggag   1320
gagatgacca gaaccaggt cagcctgacc tgcctggtca aaggcttcta tcccagcgac   1380
atcgccgtgg agtgggagag caatgggcag ccggagaaca actacaagac cacgcctccc   1440
gtgctggact ccgacggctcc cttcttcctc tacagcaagc tcaccgtgga caagagcagg   1500
tggcagcagg ggaacgtctt ctcatgctcc gtgatgcatg aggctctgca caaccactac   1560
acgcagaaga gcctctccct gtctccgggt aaa                                1593
```